US011369686B2

(12) United States Patent
Kawashima et al.

(10) Patent No.: US 11,369,686 B2
(45) Date of Patent: Jun. 28, 2022

(54) MEMBRANE FOR STICKING TO LIVING ORGANISM, AND METHOD FOR PRODUCING SAME

(71) Applicant: Panasonic Intellectual Property Management Co., Ltd., Osaka (JP)

(72) Inventors: Tomoko Kawashima, Osaka (JP); Haruka Kusukame, Nara (JP); Takahiro Aoki, Osaka (JP); Yuko Taniike, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 80 days.

(21) Appl. No.: 16/260,638

(22) Filed: Jan. 29, 2019

(65) Prior Publication Data

US 2019/0167798 A1    Jun. 6, 2019

Related U.S. Application Data

(63) Continuation of application No. PCT/JP2017/028393, filed on Aug. 4, 2017.

(30) Foreign Application Priority Data

Nov. 18, 2016 (JP) .............................. JP2016-225001

(51) Int. Cl.
| | | |
|---|---|---|
| *A61K 9/70* | (2006.01) | |
| *A61K 47/38* | (2006.01) | |
| *C08L 1/02* | (2006.01) | |
| *A61L 27/20* | (2006.01) | |
| *A61Q 19/00* | (2006.01) | |
| *A61K 8/02* | (2006.01) | |
| *A61K 8/73* | (2006.01) | |
| *B32B 23/00* | (2006.01) | |
| *C08J 5/18* | (2006.01) | |
| *A61L 15/00* | (2006.01) | |
| *C08B 16/00* | (2006.01) | |

(52) U.S. Cl.
CPC ............ *A61K 47/38* (2013.01); *A61K 8/0216* (2013.01); *A61K 8/731* (2013.01); *A61L 15/00* (2013.01); *A61L 27/20* (2013.01); *A61Q 19/00* (2013.01); *B32B 23/00* (2013.01); *C08B 16/00* (2013.01); *C08J 5/18* (2013.01); *C08L 1/02* (2013.01); *C08J 2301/02* (2013.01); *C08L 2203/02* (2013.01); *Y02P 20/54* (2015.11)

(58) Field of Classification Search
CPC .................................................... A61K 9/7076
See application file for complete search history.

(56) References Cited

U.S. PATENT DOCUMENTS

| | | | |
|---|---|---|---|
| 5,800,832 A | 9/1998 | Tapolsky et al. | |
| 9,010,547 B2 | 4/2015 | Chu et al. | |
| 2004/0029750 A1 | 2/2004 | Schudel et al. | |
| 2007/0006774 A1 | 1/2007 | Rogers et al. | |
| 2008/0254105 A1* | 10/2008 | Tapolsky | ................ A61P 23/02 424/447 |
| 2009/0078640 A1 | 3/2009 | Chu et al. | |
| 2015/0209243 A1 | 7/2015 | Shiroya et al. | |
| 2019/0328623 A1 | 10/2019 | Kame et al. | |
| 2021/0008001 A1* | 1/2021 | Namigata | ................ A61K 8/86 |

FOREIGN PATENT DOCUMENTS

| | | |
|---|---|---|
| CN | 101258196 A | 9/2008 |
| CN | 101720257 A | 6/2010 |
| EP | 2860307 A1 | 4/2015 |
| EP | 3064534 A1 | 9/2016 |
| JP | 2001-172301 | 6/2001 |
| JP | 2004-513220 | 4/2004 |
| JP | 3964465 B2 | 8/2007 |
| JP | 2009-221391 | 10/2009 |
| JP | 2010-527772 | 8/2010 |
| JP | 2012-025704 | 2/2012 |
| JP | 2014-227389 | 12/2014 |
| JP | 2015-512863 | 4/2015 |
| WO | 2007/005388 A2 | 1/2007 |
| WO | 2009/025900 A2 | 2/2009 |
| WO | WO-2009025900 A2 * | 2/2009 ............. B01D 69/12 |
| WO | 2018/168518 A1 | 9/2018 |

OTHER PUBLICATIONS

Park et al. (Biotechnology for Biofuels 2010, 3:10). (Year: 2010).*
Pang et al. (Comparison of physical properties of regenerated cellulose films fabricated with different cellulose feedstock in ionic liquid; Carbohydrate Polymers, 121, 71-78, 2015) (Year: 2015).*
Cameochemicals: Cellulose (Year: 2016).*
International Search Report of PCT application No. PCT/JP2017/028393 dated Oct. 3, 2017.

(Continued)

*Primary Examiner* — Micah Paul Young
(74) *Attorney, Agent, or Firm* — McDermott Will & Emery LLP

(57) ABSTRACT

A cellulose membrane according to an embodiment of the present disclosure is a self-supporting cellulose membrane having a thickness of between 20 nm and 1300 nm, inclusive, composed of regenerated cellulose having a weight average molecular weight of 150,000 or more.

11 Claims, 9 Drawing Sheets

(56) References Cited

OTHER PUBLICATIONS

Sunkyu Park et al., "Cellulose crystallinity index: measurement techniques and their impact on interpreting cellulase performance". Biotechnology for Biofuels 2010, 3:10.
The Extended European Search Report dated Nov. 25, 2019 for the related European Patent Application No. 17872756.6.
Kazutaka Ohira et al : "Amino Acid Ionic Liquid as an Efficient Cosolvent of Dimethyl Sulfoxide to Realize Cellulose Dissolution at Room Temperature",Chemistry Letters,vol. 41, No. 9 ,Sep. 5, 2012 (Sep. 5, 2012), pp. 987-989, XP055630857.
Communication pursuant to Article 94(3) EPC dated Nov. 12, 2020 for the related European Patent Application No. 17872756.6.
English Translation of Chinese Search Report dated Dec. 16, 2021 for the related Chinese Patent Application No. 201780030003.1.

* cited by examiner

MEMBRANE FOR STICKING TO LIVING ORGANISM, AND METHOD FOR PRODUCING SAME

TECHNICAL FIELD

The present disclosure relates to a membrane for sticking to living organism, composed of regenerated cellulose.

BACKGROUND ART

Cellulose is an organic polymer that abundantly exists in nature, and is a polymer material that is available at low cost. Cellulose has various useful characteristics including hydrophilicity, insolubility to water, and biological compatibility. Therefore, cellulose has been broadly used for example, for fibers of cloths, and separation membranes such as a dialysis membrane, and further application is expected.

As a method of processing cellulose, a method of obtaining regenerated cellulose after dissolving cellulose in an acid aqueous solution or an alkali aqueous solution or an organic solvent containing a metal salt is known. However, cellulose is difficult to be solved because cellulose forms a hydrogen bond inside the molecule or between molecules, and it has been especially difficult to obtain a solution of cellulose having a high molecular weight.

In recent years, ionic liquid receive attention as a solvent capable of efficiently dissolving cellulose. An ionic liquid is capable of dissolving more cellulose in a shorter time. For example, PTL 1 discloses a technique of forming a separation membrane by coating a porous support with a solution of cellulose in an ionic liquid.

PTL 2 discloses a technique of a dermatologic self-supporting cosmetic sheet that includes a biocompatible and/or biodegradable hydrophobic polymer layer.

CITATION LIST

Patent Literature

PTL 1: Japanese Translation of PCT Publication No. 2010-527772
PTL 2: Unexamined Japanese Patent Publication No. 2014-227389

Non-Patent Literature

NPL 1: Park et al. "Cellulose crystallinity index: measurement techniques and their impact on interpreting cellulase performance" Biotechnology for Biofuels 2010, 3 10

SUMMARY OF THE INVENTION

Technical Problem

However, a stable self-supporting thin membrane of cellulose having a thickness of about several micrometers has not been obtained yet. In the separation membrane of PTL 1, a coating layer containing cellulose is formed on a porous support, so that it is difficult to separate a cellulose membrane as a simple substance from the porous support.

Solution to Problem

As an exemplary embodiment of the present disclosure, there is provided a membrane for sticking to living organism that is self-supporting and designed for sticking to living organism, the membrane being composed of regenerated cellulose having a weight average molecular weight of 150,000 or more, and having a thickness between 20 nm and 1300 nm, inclusive.

A comprehensive or specific aspect may be realized by a membrane, a multilayer sheet or a method. A comprehensive or specific aspect may be realized by any combination of a membrane, a multilayer sheet and a method.

Additional effects and advantages of disclosed embodiments will be apparent from the description and drawings. Effects and/or advantages are provided individually by various embodiments or characteristics disclosed in the description and drawings, that are not entirely required for obtaining one or more of these.

Advantageous Effect of Invention

According to an embodiment of the present disclosure, there is provided a self-supporting membrane for sticking to living organism.

DESCRIPTION OF EMBODIMENTS

Figure 1:
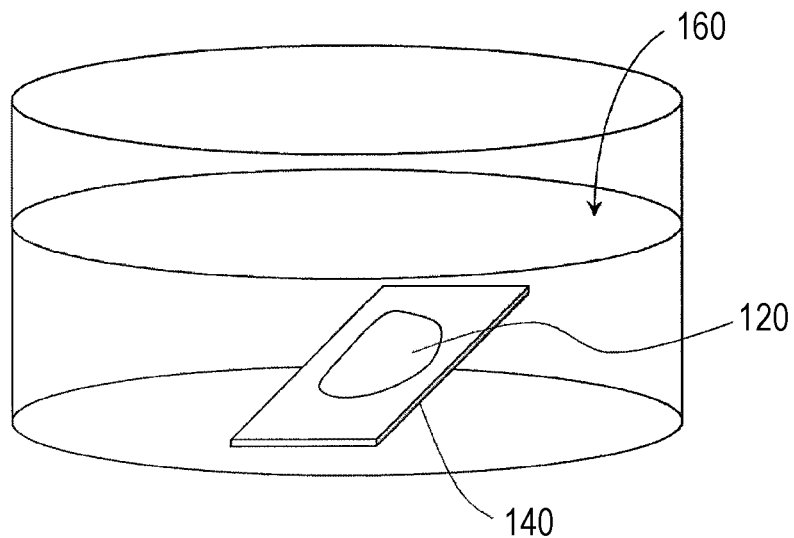
FIG. 1 is a view schematically showing the state that polymer gel sheet 120 on substrate 140 is immersed in liquid that fails to dissolve cellulose 160.

Outlines of aspects of the present disclosure are as follows.

[Item 1]

A membrane for sticking to living organism that is self-supporting and designed for sticking to living organism, the membrane being composed of regenerated cellulose having a weight average molecular weight of 150,000 or more, and having a thickness of between 20 nm and 1300 nm, inclusive.

[Item 2]

The membrane for sticking to living organism according to item 1, having an area of $7$ mm$^2$ or more.

[Item 3]

The membrane for sticking to living organism according to item 1 or 2, having a tensile strength of 23 MPa or more.

[Item 4]

The membrane for sticking to living organism according to any one of items 1 to 3, having a water vapor transmission rate of $1 \times 10^4$ g/m$^2 \cdot 24$ h or more.

[Item 5]

The membrane for sticking to living organism according to any one of items 1 to 4, having a contact angle with water of 30° or less.

[Item 6]

The membrane for sticking to living organism according to any one of items 1 to 5, having a degree of crystallinity of between 0% and 12%, inclusive.

[Item 7]

The membrane for sticking to living organism according to any one of items 1 to 6, having a bulk density of between 0.3 g/cm$^3$ and 1.5 g/cm$^3$, inclusive.

[Item 8]

The membrane for sticking to living organism according to any one of items 1 to 7, wherein a component acting on living organism or a component protecting living organism is retained by at least part inside the membrane.

[Item 9]

The membrane for sticking to living organism according to any one of items 1 to 8, wherein a coloring component is retained by at least a part inside the membrane, and the membrane is used as cosmetics or medical supplies.

[Item 10]

A multilayer sheet including:

the membrane for sticking to living organism according to any one of items 1 to 9; and a first protective layer disposed on one of principal surfaces of the membrane for sticking to living organism, the first protective layer being detachable from the one of principal surfaces.

[Item 11]

The multilayer sheet according to item 10, further including: a second protective layer disposed on the other of the principal surfaces of the membrane for sticking to living organism.

[Item 12]

A method for producing a membrane for sticking to living organism, the method including:

step (A) of preparing a cellulose solution containing a first solvent containing at least ionic liquid, and cellulose having a weight average molecular weight of 150,000 or more;

step (B) of applying the cellulose solution to a surface of a substrate having a contact angle with water of 70° or less to form a liquid membrane on the surface;

step (C) of immersing the liquid membrane in a liquid that fails to dissolve cellulose; and step (D) of removing the first solvent and the part other than the ionic liquid of the liquid from the liquid membrane, after the step (C).

[Item 13]

The method for producing a membrane for sticking to living organism according to item 12, wherein the step (B) includes step (B1) of preparing the substrate by subjecting a polymer material to surface modification.

[Item 14]

The method for producing a membrane for sticking to living organism according to item 12 or 13, wherein the step (A) further includes step (Aa) of diluting the cellulose solution.

[Item 15]

The method for producing a membrane for sticking to living organism according to item 14, wherein the step (Aa) is a step that is carried out by diluting a mixture of ionic liquid, or the first solvent and the cellulose having a weight average molecular weight of 150,000 or more, in a second solvent.

[Item 16]

The method for producing a membrane for sticking to living organism according to any one of items 12 to 15, wherein a part other than the ionic liquid in the solvent contained in the cellulose solution includes an aprotic polar solvent having a SP value of 12 or more.

[Item 17]

The method for producing a membrane for sticking to living organism according to item 16, wherein the aprotic polar solvent is dimethyl sulfoxide.

[Item 18]

The method for producing a membrane for sticking to living organism according to any one of items 12 to 17, further comprising step (E) of heating the liquid membrane, before the step (C).

[Item 19]

The method for producing a membrane for sticking to living organism according to item 18, wherein heating in the step (E) is carried out at a temperature lower than a decomposition temperature of the ionic liquid in the first solvent.

[Item 20]

The method for producing a membrane for sticking to living organism according to any one of items 12 to 19, further comprising step (F) of gelating the liquid membrane, after the step (B).

[Item 21]

The method for producing a membrane for sticking to living organism according to any one of items 12 to 20, wherein an anion contained in the ionic liquid is amino acid.

[Item 22]

The method for producing a membrane for sticking to living organism according to item 21, wherein the amino acid has a terminal carboxyl group and a terminal amino group.

[Item 23]

The method for producing a membrane for sticking to living organism according to item 21 or 22, wherein a cation contained in the ionic liquid is a quaternary ammonium cation.

[Item 24]

The method for producing a membrane for sticking to living organism according to any one of items 12 to 23, wherein the step (C) is carried out under application of voltage to the liquid.

[Item 25]

The method for producing a membrane for sticking to living organism according to item 24, wherein the voltage is lower than a voltage at which the liquid is electrolyzed.

[Item 26]

The method for producing a membrane for sticking to living organism according to any one of items 12 to 25, further comprising step (G) of immersing a membrane obtained in the step (D) in a solution containing a component that acts on living organism or a component that protects living organism, followed by drying.

Hereinafter, embodiments of the present disclosure will be specifically described by referring to drawings. In the following embodiments, comprehensive or specific examples are shown in any embodiment. The numerical values, materials, constituents, arrangements and connection forms of constituents, steps, orders of steps and the like are merely illustrative, and are not intended to limit the present disclosure. Various aspects described in the present description can be mutually combined unless a contradiction arises. Among the constituents in the following embodiments, a constituent that is not described in an independent claim showing the highest conception is described as an optional constituent. In the following description, constituents having substantially the same function are denoted by a common reference numeral, and repeated description is sometimes omitted. Graphic Illustration of part of elements is sometimes omitted so as to prevent excess complication of the drawing.

(Embodiment of Self-Supporting Cellulose Membrane)

A cellulose membrane according to an embodiment of the present disclosure is a cellulose membrane composed of regenerated cellulose having a weight average molecular weight of 150,000 or more. The cellulose membrane according to an embodiment of the present disclosure is a self-supporting thin membrane having a thickness of between 20 nm and 1300 nm, inclusive.

Figure 17:
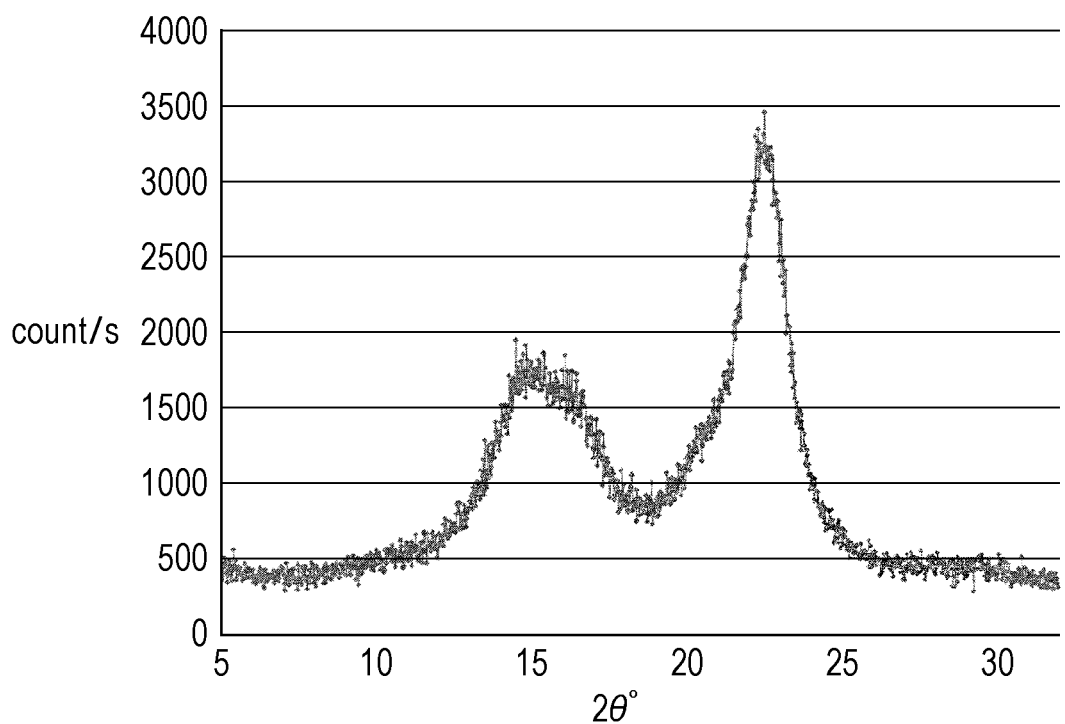
FIG. 17 is a view showing an example of XRD pattern of natural cellulose.

In the present description, "self-supporting membrane" means a membrane capable of keeping the form of the membrane without a support, and means such a membrane that when a part of the membrane is held with, for example, fingers or tweezers, and the membrane is lifted, the entire membrane can be lifted without a support while the membrane is not damaged. In the present description, "regenerated cellulose" means cellulose lacking a crystal structure I that is peculiar to natural cellulose. The crystal structure of cellulose can be confirmed by an XRD pattern. FIG. 17 shows an example of an XRD pattern (CuKα ray (50 kV, 300 mA)) of natural cellulose. In the XRD pattern shown in FIG. 17, peaks around 14-17° and 23°, that are peculiar to the crystal structure I appear. Regenerated cellulose often has a crystal structure II, and has peaks around 12°, 20° and 22°, and does not have peaks around 14-17° and 23°.

It is preferred that regenerated cellulose in the cellulose membrane in the present disclosure is not chemically modified or derivatized for 90% or more of the regenerated cellulose, more preferably for 98% or more of the regenerated cellulose. Regenerated cellulose in the cellulose membrane may not be cross-linked.

As will be described later, the cellulose membrane according to an embodiment of the present disclosure can be used while it is stuck to skin of, for example, a face, an arm or the like. The cellulose membrane according to an embodiment of the present disclosure typically has an area of 7 mm$^2$ or more. The area of the cellulose membrane of 7 mm$^2$ or more is advantageous because a large region can be covered when the membrane is stuck to the skin. Also, the cellulose membrane of the present disclosure can be applied to living organism other than skin, and for example, the cellulose membrane can be stuck to the surface of an organ for preventing adhesion between organs or for protection.

The cellulose membrane according to an embodiment of the present disclosure can have a degree of crystallinity of between 0% and 12%, inclusive. According to an illustrative production method as will be described later, it is also possible to obtain a cellulose membrane having a degree of crystallinity of 0%. When the degree of crystallinity is 12% or less, the rate of the hydroxyl groups involved in formation of the crystal form is reduced, so that the adhesiveness to skin of the cellulose membrane can be improved. Also, it is possible to add various functions to the cellulose membrane, for example, by modification at a position of the hydroxyl group.

The cellulose membrane according to an embodiment of the present disclosure has, for example, a bulk density of between 0.3 g/cm$^3$ and 1.5 g/cm$^3$, inclusive. A bulk density of 0.3 g/cm$^3$ or more is advantageous because the strength required for keeping the shape of the cellulose membrane can be ensured. When the cellulose membrane is stuck to the skin, a liquid such as water or a toning lotion or cream is sometimes interposed between the cellulose membrane and the skin. It is also possible to make the cellulose membrane itself retain a component that acts on living organism or protects living organism, such as a cosmetic component or an active ingredient. For example, such a component can be retained in voids inside the membrane. In particular, when the cellulose membrane has a bulk density of lower than 1.5 g/cm$^3$, which is the true density of cellulose, the cosmetic component or the like can permeate in the membrane more easily. The component that acts on living organism or protects living organism, such as a cosmetic component may be retained in a solid state in voids inside the membrane, or may be dissolved and/or dispersed in a liquid, and retained in a state of dispersion or cream in voids inside the membrane.

(Method for Producing Self-Supporting Cellulose Membrane)

Hereinafter, an example of a method for producing a cellulose membrane according to an embodiment of the present disclosure will be described by referring to drawings.

First, cellulose is dissolved in a solvent to prepare a cellulose solution. In an embodiment of the present disclosure, cellulose having a weight average molecular weight of at least 150,000 or more is used as cellulose to be dissolved in a solvent from the view point of finally obtaining a cellulose membrane having a weight average molecular weight of 150,000 or more. The cellulose that can be used may be cellulose derived from plants such as pulp or cotton, or cellulose generated by organisms such as bacteria as long as the cellulose has a predetermined weight average molecular weight. By using cellulose having a weight average molecular weight of 150,000 or more, it is possible to provide regenerated cellulose membrane having a thickness of 1300 nm (1.3 μm) or less, and a self-supportable strength. It is advantageous that cellulose as a material has a concentration of impurities of 5 wt % or less.

If the weight average molecular weight is too large, the viscosity of the solution is high and processing becomes difficult. Accordingly, the regenerated cellulose in the cellulose membrane that is finally obtained has a weight average molecular weight of preferably 1,000,000 or less, more preferably 500,000 or less, further preferably 300,000 or less. A weight average molecular weight of 1,000,000 or less enables processing, and a weight average molecular weight of 500,000 or less facilitates processing, and a weight average molecular weight of 300,000 or less provides a stabler sheet with less variation.

As the solvent, a solvent containing at least an ionic liquid (hereinafter, also referred to as "first solvent") is used. By using a solvent containing at least an ionic liquid, it is possible to dissolve cellulose having a weight average molecular weight of 150,000 or more in a relatively short time. An ionic liquid is a salt composed of an anion and a cation, and can assume a liquid state at a temperature of 150° C. or less. As the ionic liquid that dissolves cellulose, an ionic liquid containing amino acid or alkyl phosphate ester can be used. By using such an ionic liquid as a solvent, it is possible to dissolve cellulose while suppressing decrease in molecular weight. In particular, since amino acid is a component existing in living organism, it can be said that an ionic liquid containing amino acid enables preparation of regenerated cellulose membrane that is safer to living organism.

Cellulose can be dissolved by using an ionic liquid that is preliminarily diluted in a solvent that fails to make cellulose precipitate. For example, as the first solvent, a mixture of an aprotic polar solvent and an ionic liquid may be used. A protonic solvent makes cellulose precipitate because a hydrogen bond is easily formed in the protonic solvent. Therefore, an aprotic polar solvent is more suited from the view point of diluting the cellulose solution stably. As a solvent for dilution, it is possible to use an aprotic polar solvent having a SP (Solubility Parameter) value of 12 or more. Here, the SP value is a Hildebrand's solubility parameter calculated from molar heat of vaporization according to the regular solution theory. Examples of the aprotic polar solvent having an SP value of 12 or more include dimethyl sulfoxide. By using an ionic liquid that is preliminarily diluted, it is possible to dissolve cellulose in a short time. In particular, by setting the percentage of the ionic liquid in the first solvent to be 50 wt % or more, the effect of improving the solubility of cellulose can be obtained.

Examples of the ionic liquid that dissolves cellulose include an ionic liquid represented by the following general formula (s1). The ionic liquid represented by the general formula (s1) is an example in which the anion is amino acid. As can be seen from the general formula (s1), the anion includes a terminal carboxyl group and a terminal amino group in this example. A cation of the ionic liquid represented by the general formula (s1) may be a quaternary ammonium cation.

[Chemical formula 1]

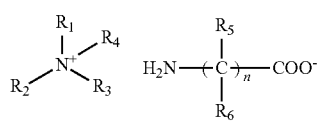

(s1)

In the general formula (s1), $R_1$ to $R_6$ each independently represent a hydrogen atom or a substituent. The substituent can be an alkyl group, a hydroxyalkyl group or a phenyl group, and may contain a branch in the carbon chain. The substituent may contain an amino group, a hydroxyl group, a carboxyl group and so on.

Alternatively, as the ionic liquid that dissolves cellulose, an ionic liquid represented by the following general formula (s2) can also be used. In the following general formula (s2), $R_1$, $R_2$, $R_3$ and $R_4$ each independently represent a hydrogen atom or a C1-C4 alkyl group.

[Chemical formula 2]

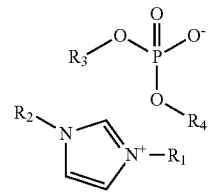

(s2)

In the step of preparing a cellulose solution, the cellulose solution may be diluted. For example, a mixture of cellulose having a weight average molecular weight of 150,000 or more and the first solvent may be diluted in the second solvent. As the second solvent, a solvent that fails to make cellulose precipitate can be used, and for example, an aprotic polar solvent having a SP value of 12 or more can be used.

The concentration of cellulose in the cellulose solution typically ranges from 0.2 wt % to 15 wt %, inclusive. By setting the concentration of cellulose to be 0.2 wt % or more, the strength required for keeping the shape of the thin membrane can be ensured in the finally obtained cellulose membrane. By adjusting the concentration of cellulose to be 15 wt % or less, it is possible to suppress precipitation of cellulose. The concentration of cellulose in the cellulose solution more preferably ranges from 1 wt % to 10 wt %, inclusive. The concentration of cellulose of 1 wt % or more is advantageous because a cellulose membrane having a hither strength can be formed. When the concentration of cellulose is 10 wt % or less, it is possible to prepare a stabler solution with less precipitation of cellulose.

Dilution lowers the viscosity of the cellulose solution and thus improves the fluidity. From the view point of stably forming a liquid membrane in the subsequent step of forming a liquid membrane, and suppressing unevenness of the surface of the liquid membrane, it is advantageous to set the concentration of cellulose to be, for example, 5 wt % or less. By suppressing unevenness of the surface of the liquid membrane, it is possible to form a cellulose membrane having a uniform thickness. Even if the concentration of cellulose is 5 wt % or less before dilution, lowering the concentration of the ionic liquid by dilution can decrease the viscosity of the cellulose solution and provide the effect of suppressing unevenness of the surface of the liquid membrane.

Next, by applying the cellulose solution on the surface of the substrate having a contact angle with water of 70° or less, a liquid membrane is formed on the surface of the substrate. When the contact angle with water is more than 70°, the surface of the substrate repels the cellulose solution, so that it is difficult to form a continuous liquid membrane stably. By using the substrate having a contact angle with water of 70° or less, it is possible to form a liquid membrane containing cellulose on the substrate.

As the substrate, a substrate having a highly hydrophilic surface can be used. The material of the substrate is not particularly limited as long as the substrate has a contact angle with water of 70° or less. However, it is to be noted that application of the cellulose solution on a porous support makes it difficult to separate the cellulose membrane from the support in the later step because the cellulose solution can permeate inside the support. Members having such a porous structure that the cellulose solution permeates inside, such as a porous support or non-woven fabric, are excluded from the "substrate" in the present description.

A substrate that is modified to have a contact angle with water of 70° or less by chemical or physical surface modification may be used. For example, a substrate made of a polymer material having subjected to UV irradiation, a corona treatment or the like may be used. Application of the surface modification makes it possible to use a flexible substrate composed of a material that is low in cost and suited for mass production, such as polypropylene (PP), for example. The technique for the surface modification is not limited to UV irradiation and a corona treatment, but application of a surface modifier, surface modification, a plasma treatment, sputtering, etching, blast or the like may be employed.

For formation of a liquid membrane, for example, gap coating, slot die coating, spin coating, coating using a bar coater (metering rod coating), gravure coating, or the like is employable. The gap coating and the slot die coating are advantageous because they can form a liquid membrane stably in the case where the cellulose solution has high viscosity, and they are easy to maintain. By adjusting the size of opening of the gap or slot die, or adjusting the concentration of the cellulose solution, it is possible to adjust the thickness of the finally obtainable cellulose membrane. Alternatively, for formation of a liquid membrane, a casting method, screen printing using a squeegee, or blast painting, electrostatic spraying or the like may be employed.

A liquid membrane may be formed while the cellulose solution and/or the substrate are heated. By the heating, the fluidity of the cellulose solution improves, so that the effect of reducing the variation in thickness of the liquid membrane is obtained. Heating is carried out within a temperature range (for example, 40° C. to 100° C.) where the cellulose solution can be kept stably.

The liquid membrane may be heated after formation of the liquid membrane. Heating after formation of the liquid membrane is carried out at a temperature that is lower than the decomposition temperature of the ionic liquid in the first solvent (for example, about 70° C. to 200° C.). Heating may be carried out at a temperature that is lower than the decomposition temperature of the ionic liquid, and is lower than the boiling point of the second solvent used for diluting a mixture of cellulose and the first solvent. By carrying out the heating within the temperature range as described above, it is possible to appropriately remove the solvent other than the ionic liquid (for example, dimethyl sulfoxide), and to form a regenerated cellulose thin membrane having high strength. Also, deterioration in properties of the cellulose membrane caused by bumping of the solvent in the cellulose solution can be suppressed. Heating may be carried out in a reduced-pressure environment. The reduced pressure makes it possible to moderately remove the solvent other than the ionic liquid at a temperature lower than the boiling point in a shorter time.

The liquid membrane may be gelated after formation of the liquid membrane. By exposing the liquid membrane to a vapor of the liquid that is soluble to the ionic liquid but fails to dissolve cellulose, it is possible to gelate the liquid membrane to obtain a polymer gel sheet. For example, when the liquid membrane is left to stand in an environment at a relative humidity of 30 to 100% RH, the ionic liquid is contaminated with water, so that the solubility of cellulose decreases, the cellulose molecule partly precipitates to form a three-dimensional structure, and finally the liquid membrane is gelated. The gel point can be recognized according to whether the membrane of the gel can be lifted up or not.

The degree of crystallinity of the finally obtainable cellulose membrane can be adjusted by the condition of the gelation. For example, when gelation is carried out in an environment at a relative humidity of 60% RH or less, the gelation advances gradually, so that a three-dimensional structure of cellulose molecule is easy to be formed stably and the degree of crystallinity can be reduced stably. In an environment at a relative humidity of 40% RH or less, it is possible to obtain a regenerated cellulose membrane having a further reduced degree of crystallinity. Here, an example of forming a polymer gel sheet and finally obtaining a regenerated cellulose membrane is described. The aforementioned heating step may be carried out before or after the step of gelating a liquid membrane, or may be carried out before and after the step of gelating a liquid membrane.

Next, as schematically shown in FIG. 1, polymer gel sheet 120 on substrate 140 is immersed in liquid 160 that fails to dissolve cellulose (hereinafter, also referred to as "rinsing liquid"). This step can also be referred to as a step of washing the polymer gel sheet for removing the ionic liquid from the polymer gel sheet. At this time, the part other than cellulose and the ionic liquid (for example, the second solvent) in the cellulose solution may partly be removed together with the ionic liquid.

In this step, rinsing liquid 160 may be replaced a plurality of times. As liquid (rinsing liquid) 160 in which a polymer gel sheet is to be immersed, a solvent that is soluble at least to an ionic liquid can be used. Examples of such a liquid include water, methanol, ethanol, propanol, butanol, octanol, toluene, xylene, acetone, acetonitrile, dimethylacetamide, dimethylformamide, and dimethyl sulfoxide. From the view point of ease of handling, it is advantageous to use water, ethanol.

Figure 2:
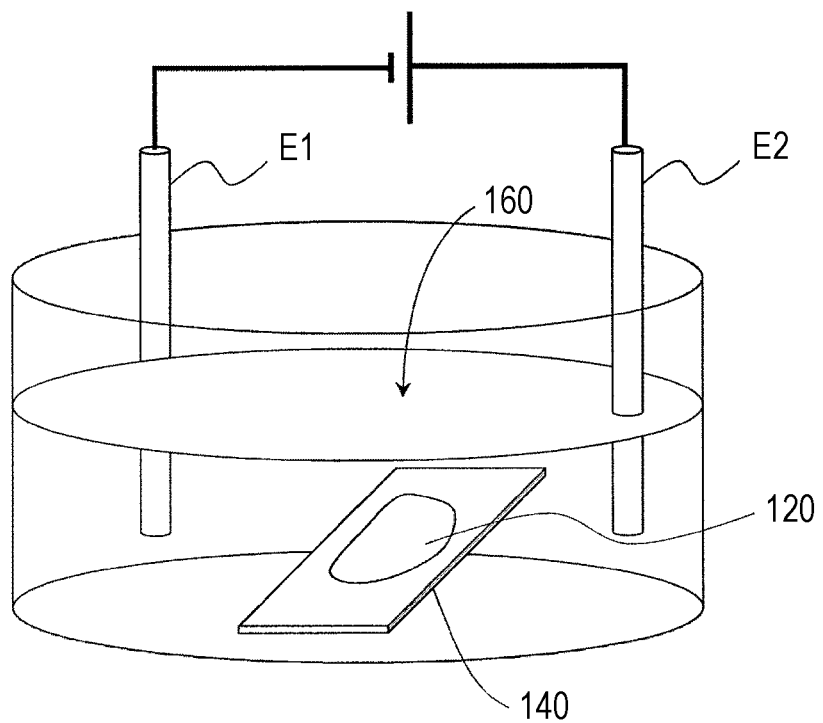
FIG. 2 is a view schematically showing a configuration in which electrodes E1, E2 are disposed in liquid 160 that fails to dissolve cellulose.

In immersion of polymer gel sheet 120 in rinsing liquid 160, electrodes E1, E2 may be arranged in rinsing liquid 160 and a voltage may be applied between these electrodes as schematically shown in FIG. 2. Application of the voltage makes it possible to remove the ionic liquid from polymer gel sheet 120 in a short time by the electric action. Therefore, the effect of improving the productivity such as cost reduction is obtained. The voltage applied at this time is a voltage that is lower than the voltage at which rinsing liquid 160 is electrolyzed in consideration of the possible influence on properties of the cellulose membrane by excessive voltage.

After the step of immersing the polymer gel sheet, the solvent or the like is removed from the polymer gel sheet. In other words, the polymer gel sheet is dried. At this time, it is advantageous to dry the polymer gel sheet while the polymer gel sheet is placed on a nonwoven fabric or the like because the polymer gel sheet after drying can be easily separated from the nonwoven fabric. As a drying method, various drying methods such as natural drying, vacuum drying, heat drying, freeze-drying, supercritical drying and the like can be employed. Vacuum heating may be conducted. The conditions in drying are not particularly limited, and time and temperature that are enough to remove the solvent used for dilution of the cellulose solution, and the rinsing liquid can be employed. By removing the solvent and the like from the polymer gel sheet, it is possible to obtain a cellulose membrane according to an embodiment of the present disclosure.

In this step, by employing natural drying, vacuum drying or heat drying, it is possible to obtain a robust cellulose membrane having relatively high bulk density. When the freeze-drying or supercritical drying is employed, there is a tendency that a cellulose membrane having a further lower bulk density is obtained compared with the case where natural drying, vacuum drying or heat drying is employed. The bulk density in the cellulose membrane can also be adjusted by the concentration of cellulose in the liquid membrane, the kind of the solvent retained by the polymer gel sheet at the time of carrying out the drying, and so on. By lowering the bulk density, it is possible to provide a cellulose membrane capable of retaining a larger amount of moisture and/or a useful component such as a cosmetic component.

When freeze-drying is employed, a solvent that is freezable and has a boiling point around 100 to 200° C. can be used. Freeze-drying can be carried out by using, for example, water, tert-butyl alcohol, acetic acid, 1,1,2,2,3,3,4-heptafluorocyclopentane, dimethyl sulfoxide or the like. It is advantageous that the solvent used in the freeze-drying is a solvent that is soluble to the rinsing liquid. Even when the solvent used in the freeze-drying is such a solvent that is soluble to the rinsing liquid, it is possible to carry out the freeze-drying by replacing the rinsing liquid in the polymer gel sheet by a solvent that is soluble to the rinsing liquid, after the step of immersing the polymer gel sheet, and further replacing the solvent with a solvent for freeze-drying.

By the steps as mentioned above, a self-supporting cellulose membrane according to an embodiment of the present disclosure is obtained. Further, it is also possible to produce a cellulose membrane retaining a cosmetic component or the like by immersing the self-supporting cellulose membrane thus obtained in a solution containing a component that acts on living organism or protects living organism, such as a cosmetic component, removing the cellulose membrane from the solution and then drying the cellulose membrane.

Figure 3:
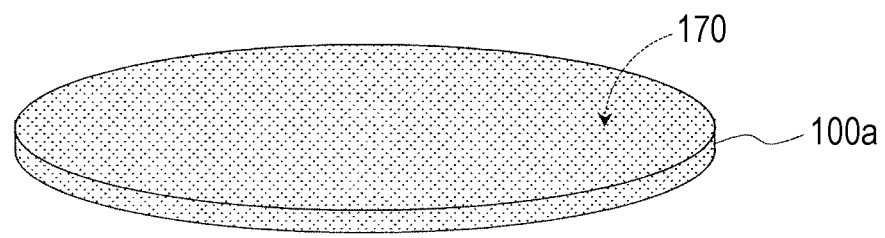
FIG. 3 is a schematic perspective view showing an example of a cellulose membrane retaining a component that acts on living organism or protects living organism.

FIG. 3 shows an example of a cellulose membrane having a component that acts on living organism or protects living organism. FIG. 3 shows cellulose membrane 100a having a generally circular shape. This is merely given for exemplification, and the shape of cellulose membrane 100a is not limited to the example shown in FIG. 3.

Cellulose membrane 100a retains cosmetic component 170, for example, inside the membrane, as a component that acts on living organism or protects living organism. The cosmetic component may exist on the surface of the membrane. Whether or not the cellulose membrane retains a useful component such as a cosmetic component can be examined, for example, by the infrared spectroscopy. Since cellulose is hydrophilic, it is possible to make the cellulose membrane according to an embodiment of the present disclosure retain a water-soluble component. Further, since cellulose molecules have amphipathicity that combines hydrophobicity and hydrophilicity, it is also possible to make the cellulose membrane retain a hydrophobic component. Examples of the water-soluble cosmetic component include hyaluronic acid, vitamin B, vitamin C, and derivatives thereof, collagen, and placenta, and examples of the hydrophobic cosmetic component include vitamin A, vitamin E, ceramide, and fullerene. The cellulose membrane is also capable of retaining a medically effective component inside the membrane, as the component that acts on living organism or protects living organism. Examples of the medically effective component include tacrolimus, isosorbide dinitrate, finasteride, and minoxidil. Also, the cellulose membrane can retain a component that protects skin, such as a sunscreen agent. The sunscreen agent includes a UV-absorbing material such as dioxybenzone, or 4-methoxycinnamic acid 2-ethylhexyl, and a UV-scattering material such as titanium oxide or zinc oxide.

According to an embodiment of the present disclosure, since cellulose having a weight average molecular weight of 150,000 or more is used, it is possible to provide a cellulose membrane capable of keeping the shape without need of a support, while having a thickness within a range about 20 nm to 1300 nm. The present inventors believes that this is because the strength along the direction in which the molecular chain extends is improved in the cellulose membrane owing to the high molecular weight of the cellulose, and more hydroxyl groups are contained per one molecular chain and more hydrogen bonds are formable between molecules because cellulose not having subjected to chemical modification, derivatization or the like is used.

Further, in an embodiment of the present disclosure, the membrane is composed of regenerated cellulose. Hydrogen bonds between nanofibers constituting fibers of the cellulose are responsible for the strength of the membrane that is formed from a suspension in which fibers of natural cellulose are dispersed in water or the like. Therefore, only a fragile cellulose membrane is obtained. On the other hand, in a membrane composed of regenerated cellulose, hydrogen bonds between cellulose molecular chains are responsible for the strength of the membrane composed of the regenerated cellulose because nanofibers are disassembled to the units of molecular chains. In other words, hydrogen bonds between units that are smaller than those in nanofibers are uniformly formed in the membrane composed of regenerated cellulose. Therefore, it is possible to provide a cellulose membrane having reduced fragility, moderate flexibility, and less likelihood of breakage compared with the case where the membrane is formed from a suspension in which fibers of natural cellulose are dispersed in water or the like. Here, "nanofiber", which is also called "nanofibril (or microcapsule)", is the most basic unit of assembled cellulose molecules, and has a width of about 4 nm to about 100 nm, and a length of, for example, about 1 μm or more.

According to an embodiment of the present disclosure, since the cellulose membrane has moderate flexibility, the cellulose membrane deforms in accordance with unevenness if the unevenness is within a certain degree, and thus the cellulose membrane can be stuck to a curved surface relatively easily.

(Application Examples)

The cellulose membrane according to an embodiment of the present disclosure has high strength, and can be used while it is stuck, for example, to skin. According to an embodiment of the present disclosure, since a cellulose membrane having moderate water vapor transmission rate can be provided, the cellulose membrane can be stuck to skin and used for a long time with suppression of occurrence of sweatiness.

Figure 4:
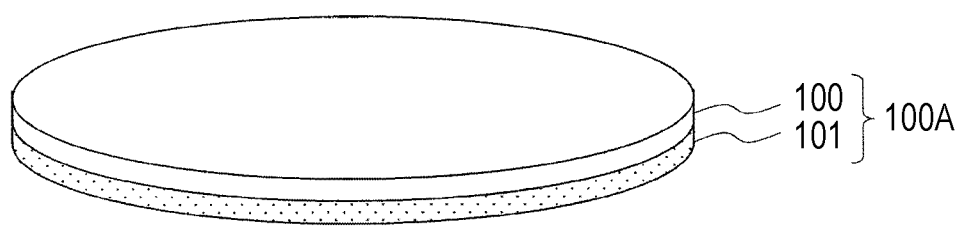
FIG. 4 is a schematic perspective view showing multilayer sheet 100A having cellulose membrane 100.
Figure 5:
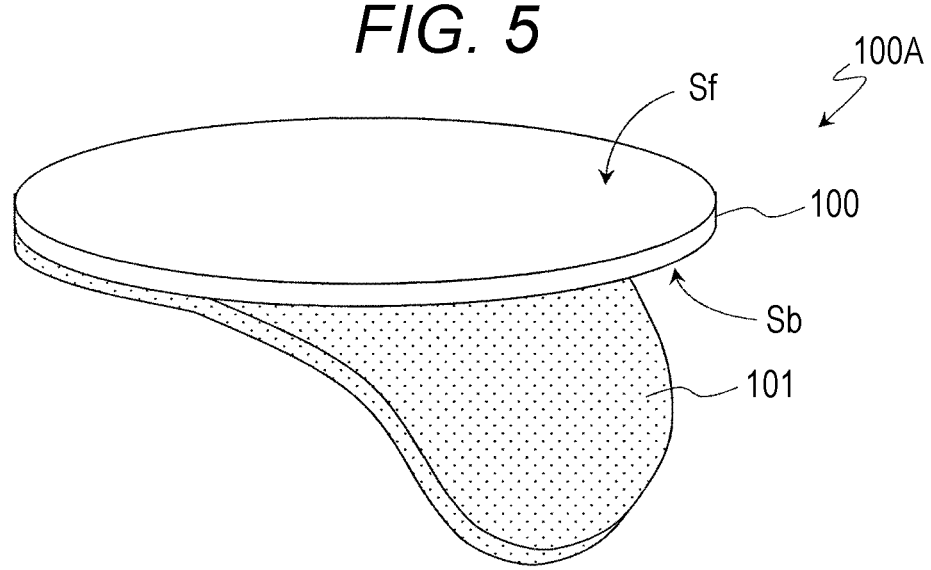
FIG. 5 is a schematic perspective view showing the state that a part of protective layer 101 is peeled off from principal surface of cellulose membrane 100.

FIG. 4 and FIG. 5 show application examples of the cellulose membrane according to an embodiment of the present disclosure. As shown in FIG. 4, cellulose membrane 100 according to an embodiment of the present disclosure can be provided in the form of a laminate having a cellulose membrane and a protective layer. Multilayer sheet 100A shown in FIG. 4 has cellulose membrane 100, and protective layer 101 disposed on one of principal surfaces of cellulose membrane 100. Cellulose membrane 100 is composed of regenerated cellulose having a weight average molecular weight of 150,000 or more. It goes without saying that FIG. 4 and FIG. 5 show multilayer sheet 100A merely schematically, and actual dimensions are not precisely reflected. For example, thicknesses of cellulose membrane 100 and protective layer 101 are exaggerated in FIG. 4 and FIG. 5. Also in other drawing of the present disclosure, the cellulose membrane or the like is sometimes depicted in a dimension or a shape that is different from the actual dimension or shape for convenience of illustration.

In this example, cellulose membrane 100 has a generally circular shape. Cellulose membrane 100 shown in FIG. 4 can have a diameter of, for example, about 3 mm. Of course, the shape of cellulose membrane 100 is not limited to the example shown in FIG. 4, but can be an ellipse, a polygon or amorphous. Cellulose membrane 100 and protective layer 101 may be different in size.

Reference is made to FIG. 5. Cellulose membrane 100 has principal surfaces Sf and Sb, and protective layer 101 is disposed on the side of principal surface Sb herein. Protective layer 101 is a sheet or a nonwoven fabric of, for example, polyethylene, polypropylene, polyethylene terephthalate, nylon, acryl resin, polycarbonate, polyvinyl chloride, acrylonitrile-butadiene-styrene (ABS) resin, polyurethane, synthetic rubber, cellulose, Teflon (registered trade name), aramid, polyimide and the like, or sheet-like metal, glass and the like. The whole or part of the surface of the sheet or the nonwoven fabric may be subjected to a chemical or physical surface treatment. In this example, protective layer 101 also has a circular shape likewise cellulose membrane 100. However, it is not necessary that cellulose membrane 100 and protective layer 101 are coincident in shape. For example, a plurality of cellulose membranes 100 can be disposed on single protective layer 101. Protective layer 101 in multilayer sheet 100A is not a support for keeping the shape of cellulose membrane 100.

As schematically shown in FIG. 5, protective layer 101 is formed so as to be peelable from principal surface Sb of cellulose membrane 100. Cellulose membrane 100 has a tensile strength of, for example, 23 MPa or more, and can keep the shape even in the state that the protective layer 101 is peeled off.

Figure 6:
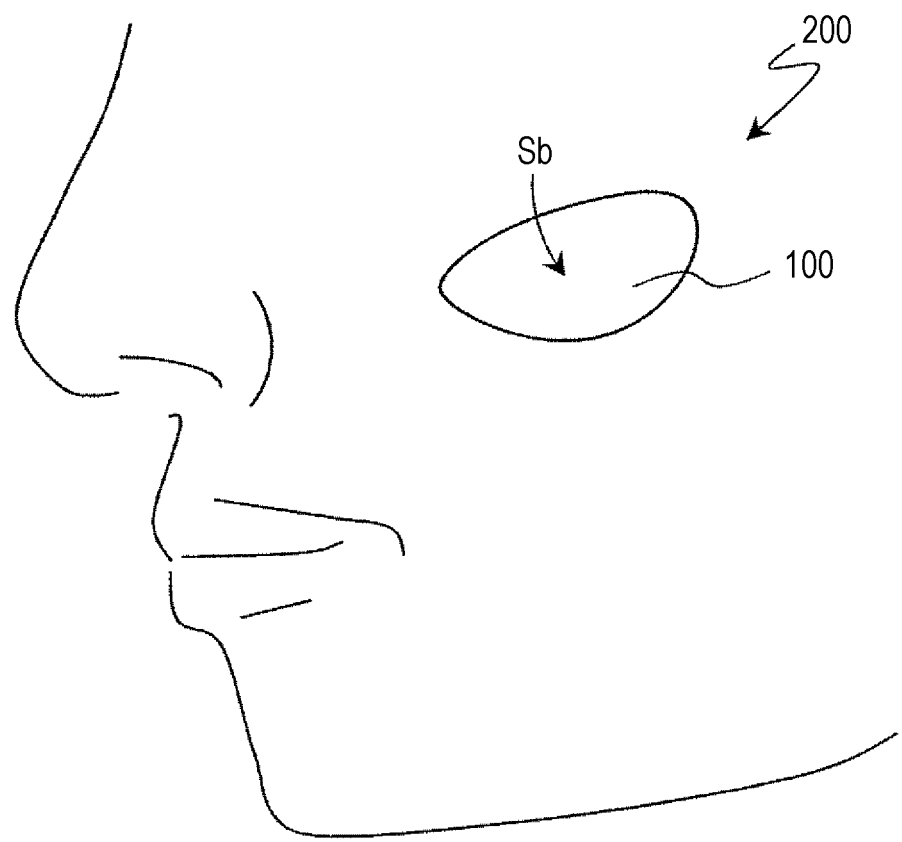
FIG. 6 is a view showing a use example in which cellulose membrane 100 is stuck to a part of the face.
Figure 7:
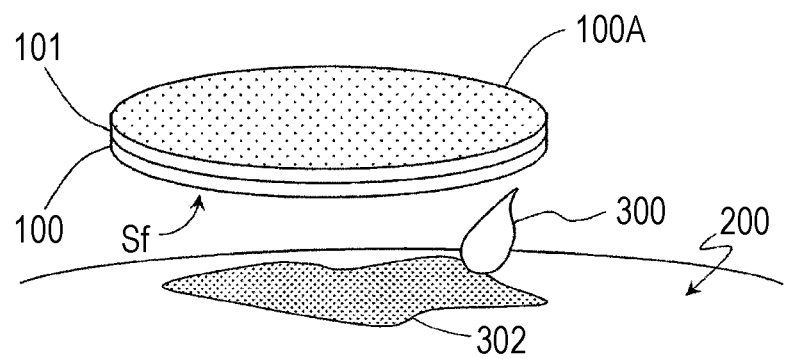
FIG. 7 is a view for illustrating an example in which liquid 300 and/or cream 302 are interposed between cellulose membrane 100 and skin 200.

FIG. 6 shows a use example of cellulose membrane 100. FIG. 6 shows the state that cellulose membrane 100 is stuck to skin 200 (herein, part of face skin). As illustrated, cellulose membrane 100 can be used while it is stuck to a part of a body, for example, face, arm or the like. Cellulose membrane 100 having a tensile strength of 23 MPa or more will not easily break even when it is stuck to skin, and cellulose membrane 100 can be stuck on the skin for a long time.

Referring to FIG. 7 to FIG. 12, an example of a method for using a multilayer sheet of the present disclosure is described.

First, multilayer sheet 100A as described above is prepared, and as shown in FIG. 7, principal surface Sf on which protective layer 101 is not disposed, of principal surfaces Sf and Sb of cellulose membrane 100 is opposed to a part where multilayer sheet 100A is intended to be stuck. In this example, principal surface Sf of cellulose membrane 100 is opposed to a part of the skin of the face (skin 200).

At this time, liquid 300 such as water and/or cream 302 may be applied on principal surface Sf of cellulose membrane 100 or on skin 200. Liquid 300 and cream 302 contain, for example, water, oils and fats, alcohol or an emulsifier or the like, and may further contain one or more components intended for cosmetics, medical care, or protection of skin, for example, collagen, hyaluronic acid, various vitamins, and derivatives thereof, ceramide, amino acid, placenta, fullerene and the like cosmetic components.

Cellulose membrane 100 may be formed of a single membrane, or may be a multilayer membrane made up of a laminate of a plurality of membranes. In the case of a multilayer membrane, cellulose membranes to be laminated may contain different components. Cellulose membrane 100 may be used as a laminate with a sheet material of other than cellulose.

Figure 8:
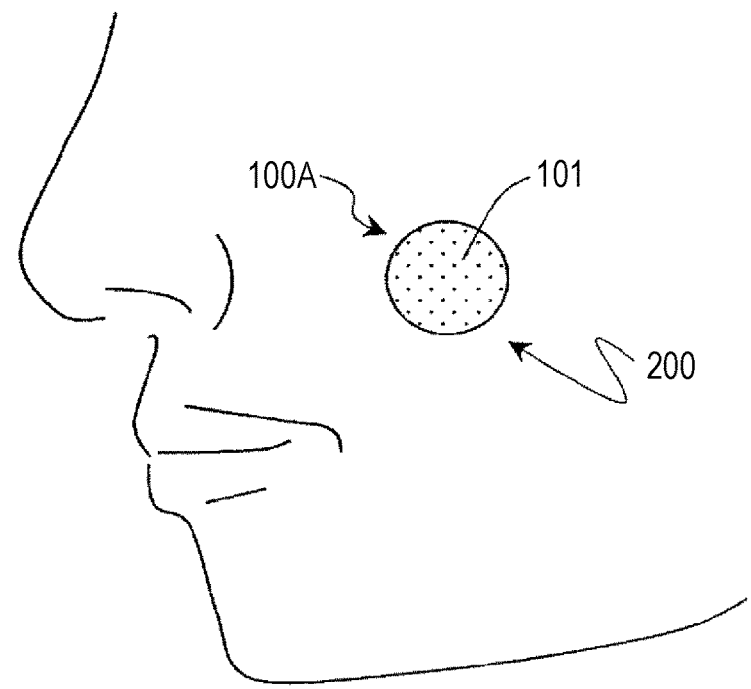
FIG. 8 is a view showing the state that multilayer sheet 100A is stuck to skin 200.
Figure 9:
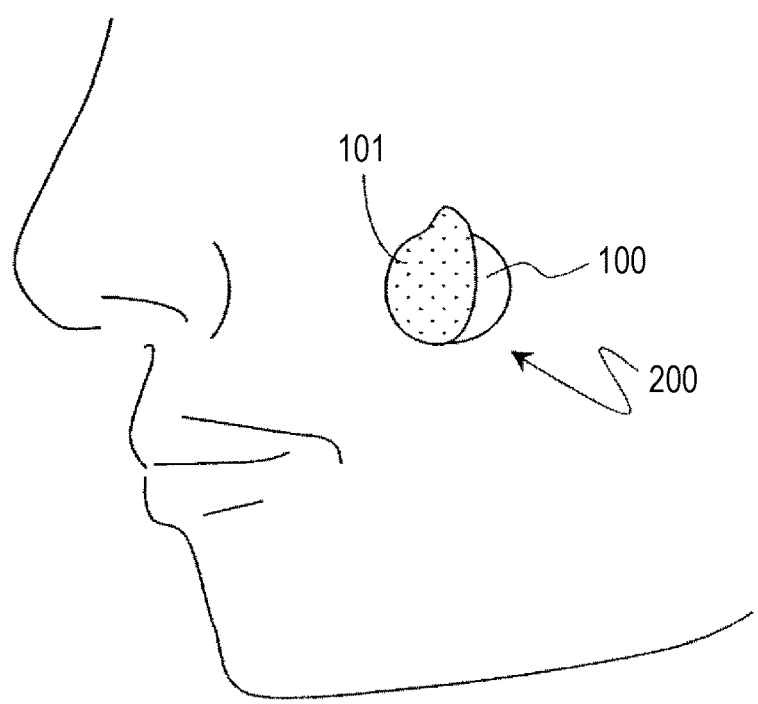
FIG. 9 is a view showing the state in the course of peeling off protective layer 101 from cellulose membrane 100 on skin 200.

Next, in the condition that principal surface Sf of cellulose membrane 100 is opposed to skin 200, multilayer sheet 100A is brought into contact with skin 200, and thus multilayer sheet 100A is stuck to skin 200 as shown in FIG. 8. Further, as shown in FIG. 9, protective layer 101 is peeled off from principal surface Sb of cellulose membrane 100. By peeling off protective layer 101 from cellulose membrane 100, it is possible to leave cellulose membrane 100 on skin 200 (see FIG. 6).

Figure 10:
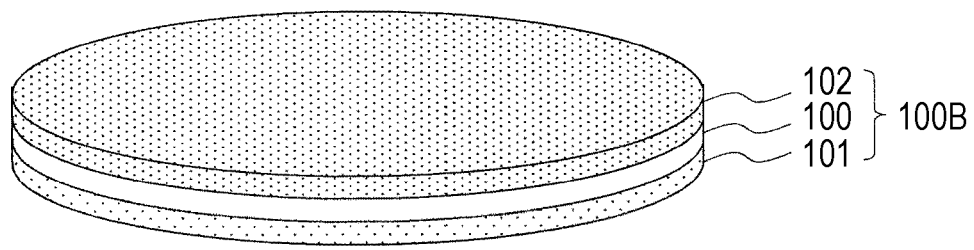
FIG. 10 is a schematic perspective view showing multilayer sheet 100B having cellulose membrane 100, protective layer 101 and second protective layer 102.

Other protective layer may be provided on principal surface Sf of cellulose membrane 100. FIG. 10 shows another example of the multilayer sheet. Multilayer sheet 100B shown in FIG. 10 has second protective layer 102 on the principal surface on the opposite side of the principal surface on which protective layer 101 is disposed, of principal surfaces of cellulose membrane 100. The material that forms protective layer 102 may be the same as or different from the material of protective layer 101. The size of protective layer 102 may be different from the size of cellulose membrane 100 or protective layer 101. Typically, also protective layer 102 can be peeled off from cellulose membrane 100 likewise protective layer 101. Existence of protective layer 102 further facilitates handling of cellulose membrane 100.

Figure 11:
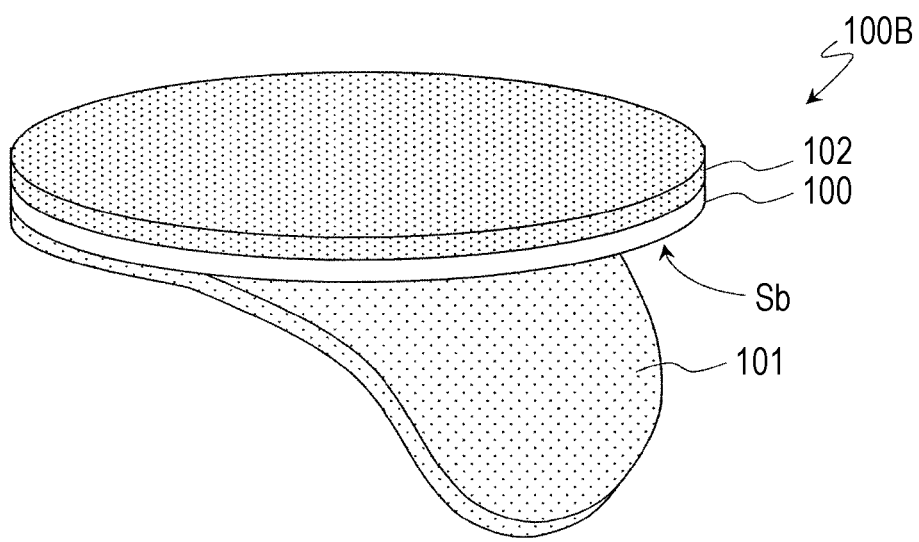
FIG. 11 is a schematic perspective view showing the state that a part of protective layer 101 is peeled off from cellulose membrane 100 of multilayer sheet 100B.

When such multilayer sheet 100B is used, first, protective layer 101 is peeled off from cellulose membrane 100 as shown in FIG. 11. Removal of protective layer 101 results in exposure of principal surface Sb of cellulose membrane 100. Thereafter, exposed principal surface Sb is opposed to skin 200. Likewise the case of multilayer sheet 100A, at this time, liquid 300 such as water or a toning lotion, and/or cream 302 may be applied on principal surface Sb of cellulose membrane 100 or on skin 200.

Figure 12:
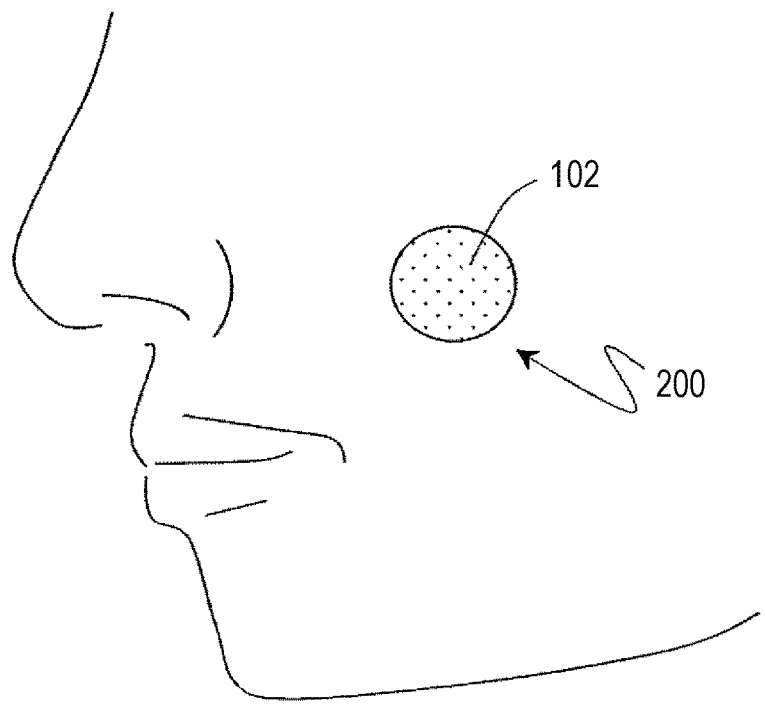
FIG. 12 is a view showing the state that a laminate of cellulose membrane 100 and second protective layer 102 is stuck to skin 200.

Next, as shown in FIG. 12, a laminate of cellulose membrane 100 and second protective layer 102 is stuck to skin 200. Thereafter, protective layer 102 is peeled off from the other of principal surfaces (principal surface opposite to principal surface Sb) of cellulose membrane 100. By peeling off protective layer 102, it is possible to leave cellulose membrane 100 on skin 200.

Figure 13:
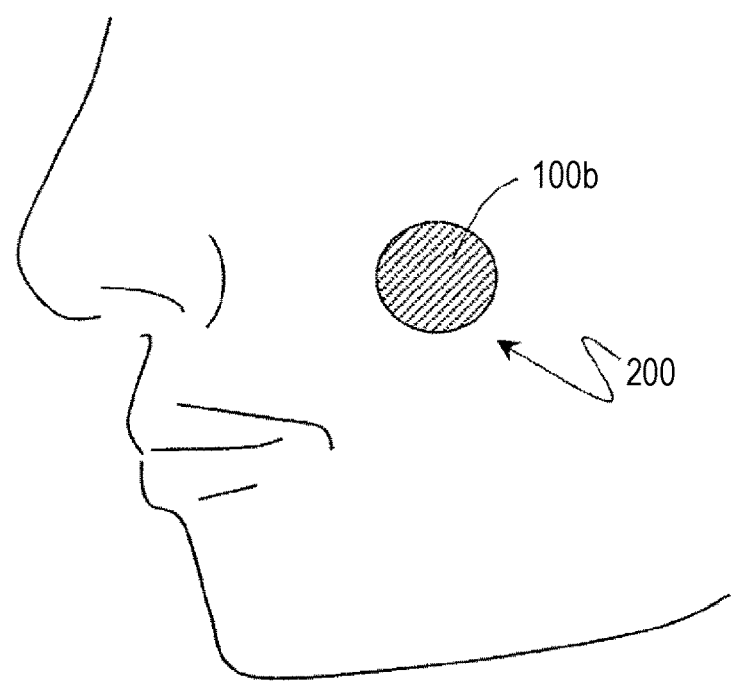
FIG. 13 is a view schematically showing the state that colored cellulose membrane 100b is stuck to skin 200.

Cellulose membrane of present disclosure may be at least partly colored. FIG. 13 schematically shows the state that colored cellulose membrane 100b is stuck to skin 200. According to the aforementioned illustrative production method, a transparent cellulose membrane is typically obtained. By using cellulose membrane 100b that is colored with a skin-like color, it is possible to cover chloasma, a mole, a scar and the like on skin 200 with cellulose membrane 100b and to make them be inconspicuous. For example, cellulose membrane 100 stuck on a scar can function as a protective sheet that protects the skin from the external stimulation. Cellulose membrane 100 may retain a component intended for medical care. Alternatively, cellulose membrane can be usable as a decorating sheet such as a rub-on tattoo when the cellulose membrane is provided with a pattern and a color by printing or the like.

Conventionally, as a material for a sheet for sticking to skin, polylactic acid has been proposed. However, polylactic acid is a hydrophobic material, and is unsuited for a long-time use because it has a fear of sweatiness. Further, a sheet of polylactic acid can require an adhesive such as an acryl adhesive or a silicone adhesive for sticking to skin if the sheet has a thickness of 500 nm or more. Therefore, in use applications for sticking to skin, it is necessary to consider stimulation of the adhesive on the skin, and the water vapor transmission rate of the adhesive.

In contrast to this, cellulose membrane 100 having a thickness of 1300 nm or less can be stuck to skin 200 without need of an adhesive. The reason why the membrane having a thickness of 500 nm or more can be stuck to skin without an adhesive is inferred as follows. Cellulose membrane 100 exhibits flexibility and easily conforms with unevenness (for example, curved surface of face, arm or the like) even when it has a thickness of 500 nm or more, and thus the influences of functional groups and van der Waals force on the surface of the cellulose membrane increase as compared with the polylactic acid membrane, so that the adhesiveness improves. Since the membrane can be stuck to skin without an adhesive, cellulose membrane 100 can be used for a long time while occurrence of sweatiness is suppressed. Further, cellulose has biocompatibility, and is less likely to add physical or chemical stress to skin even when it is directly stuck on the skin. Also since cellulose is amphipathic, and has such properties that it is insoluble to water while having hydrophilic characteristics, there is no fear of being dissolved in water such as sweat, and excellent durability is achieved.

Cellulose membrane 100 can have a WVTR (water vapor transmission rate) of $1 \times 10^4$ g/m²·24 h or more. Cellulose membrane 100 having a water vapor transmission rate of $1 \times 10^4$ g/m²·24 h or more is advantageous because uncomfortableness caused by sweatiness or the like can be reduced when cellulose membrane 100 is stuck to skin.

Cellulose membrane 100 can have a contact angle with water within the range of 0° to 30°. When cellulose membrane 100 has a contact angle within this range, the affinity between the surface of the membrane and water increases, and the cellulose membrane absorbs water on the skin quickly, so that stability and comfortableness when the sheet is stuck can be made more excellent.

Cellulose membrane 100 may have a thickness of between 50 nm and 1000 nm, inclusive. When the thickness is 50 nm or more, higher strength is obtained, and handling of cellulose membrane 100 is further facilitated. The thickness of cellulose membrane 100 of 1000 nm or less is advantageous because cellulose membrane 100 stuck to skin is inconspicuous. Cellulose membrane 100 may have a thickness of between 500 nm and 1000 nm, inclusive. When the thickness is 500 nm or more, a tear-proof cellulose membrane having higher strength is obtained. Also, it is possible to make cellulose membrane retain a larger amount of an effective component (for example, cosmetic component). Cellulose membrane 100 may have a thickness of between 100 nm and 500 nm, inclusive. A thickness of 100 nm or more is advantageous for keeping the shape of the thin membrane. By making the thickness be 500 nm or less, the adhesiveness of cellulose membrane 100 is further improved. Therefore, it is possible to stick cellulose membrane 100 to skin or other surface stably for a longer time. Also, further reduction in thickness of cellulose membrane 100 makes cellulose membrane 100 more inconspicuous on the skin.

EXAMPLES

Hereinafter, the cellulose membrane according to an embodiment of the present disclosure is described more specifically by way of examples. It goes without saying that embodiments of the present disclosure are not limited to forms specified by the following examples.

(Evaluation of Strength)

Example 1

Cellulose membrane of Example 1 was prepared in the following procedure. First, filter paper made of wood having a purity of cellulose of 99% or more was prepared. A weight average molecular weight of cellulose contained in the filter paper measured by GPC (Gel Permeation Chromatography)-MALS (Multi Angle Light Scattering) method was about 170,000.

For measurement, a liquid delivery unit LC-20AD available from Shimadzu Corporation was used, and as detectors, a differential refractometer Optilab rEX and a multi-angle light scattering detector DAWN HELEOS available from Wyatt Technology Corporation were used. As a column, TSKgel α-M available from TOSOH CORPORATION was used, and as a solvent, dimethyl acetamide to which lithium chloride was added in 0.1 M was used. The measurement was conducted at a column temperature of 23° C., and a flow rate of 0.8 mL/min.

By dissolving filter paper in an ionic liquid, a cellulose solution was prepared. As the ionic liquid, an ionic liquid in which $R_1$ is a methyl group, and $R_2$ to $R_4$ are ethyl groups in the general formula (s2) was used.

Next, a glass substrate with a flat surface having a contact angle with water of 34° was prepared. The contact angle was determined according to the θ/2 method using an automated contact angle meter DM-501 available from Kyowa Interface Science Co., LTD. Then by applying a cellulose solution on the surface of the glass substrate by gap coating, a liquid membrane was formed on the glass substrate. At this time, the size of gap was adjusted so that the thickness of the regenerated cellulose membrane was a target thickness of 200 nm.

After formation of the liquid membrane, the glass substrate and the liquid membrane were sufficiently left to stand in an environment of 25° C., 30 to 40% RH, to cause gelation of the liquid membrane, and thus a polymer gel sheet was obtained. Thereafter, the polymer gel sheet was washed with water to remove the ionic liquid from the polymer gel sheet. At this time, by immersing the glass substrate and the polymer gel sheet in ultrapure water, and replacing the ultrapure water a plurality of times, water washing of the polymer gel sheet was carried out.

The polymer gel sheet was held with tweezers and removed from the glass substrate in the ultrapure water, and placed on a nonwoven fabric. The polymer gel sheet on the nonwoven fabric was removed from the ultrapure water, and the polymer gel sheet was dried by heating at 70° C. By peeling off the dried polymer gel sheet from the nonwoven fabric, a cellulose membrane of Example 1 was obtained. The cellulose membrane of Example 1 had a shape of approximately 5 cm square, and transparent appearance.

Thickness d of the cellulose membrane of Example 1 placed on the glass substrate measured with a stylus profiling system DEKTAK (registered trade name) available from Bruker Nano Incorporated was about 210 nm. The obtained cellulose membrane had a bulk density of 1.5 g/cm³. Bulk density $d_B$ was determined according to the following formula (1). In the formula (1), W represents the mass of a test piece prepared by cutting out cellulose membrane, d represents the thickness of a test piece, and $A_p$ represents the area of a test piece.

$$d_B = W/A_p d \quad (1)$$

Degree of crystallinity of the cellulose membrane of Example 1 was determined according to the method utilizing $^{13}$C-NMR as reported by Park et al. (see NPL 1). Outline of calculating the degree of crystallinity will be described. Regarding a peak around 87 to 93 ppm as being originated from a crystal structure, and a broad peak around 80 to 87 ppm as being originated from a non-crystal structure in a spectrum acquired by solid $^{13}$C-NMR measurement, degree of crystallinity is determined from a peak area X of the former, and a peak area Y of the latter according to the following formula.

(Degree of crystallinity) %=(X/(X+Y))×100(wherein, "×" indicates multiplication.)

For measurement of $^{13}$C-NMR, Unity Inova-400 available from Varian Medical Systems, and a 5 mm CP/MAS probe available from Doty Scientific, Inc. were used, and the CP/MAS method was used. The measurement conditions were as follows: MAS speed: 10 kHz, room temperature (25° C.), number of revolutions of sample: 10 kHz, observation width: 30.2 kHz, observation center: 96 ppm, observation frequency: 100.574 MHz, and in CP pulse ($^1$H→$^{13}$C) method, observation nucleus 90° pulse: 3.9 µsec, 1H excitation pulse: 3.8 µsec, contact time: 2.0 msec, wait time: 10 sec or more, number of integration: 8,000 times. It was confirmed that the solid $^{13}$C-NMR spectrum of cellulose measured in these conditions by the CP method well coincide with the solid $^{13}$C-NMR spectrum measured by a DD (Dipolar Decouple) method in which a sufficient relaxation time is set. The calculated degree of crystallinity was 0%.

A weight average molecular weight concerning cellulose in the obtained cellulose membrane, determined in the same manner as for the cellulose used as a starting material, was about 162,000.

A contact angle with water of the cellulose membrane of Example 1 was 3°. The contact angle was determined according to the θ/2 method using an automated contact angle meter DM-501 available from Kyowa Interface Science Co., LTD.

Example 2

A cellulose membrane of Example 2 was prepared in the same manner as for the sample of Example 1 except that as the ionic liquid for dissolving cellulose, an ionic liquid in which $R_3$ is a hydrogen atom, and $R_1$, $R_2$ and $R_4$ are methyl groups in the general formula (s2) was used. The obtained cellulose membrane had a thickness d of about 190 nm and a weight average molecular weight Mw of about 152,000.

Example 3

A cellulose membrane of Example 3 was prepared in the same manner as for the sample of Example 1 except that as the ionic liquid for dissolving cellulose, an ionic liquid in which $R_3$ is a hydrogen atom, $R_1$ and $R_4$ are methyl groups, and $R_2$ is an ethyl group in the general formula (s2) was used. The obtained cellulose membrane had a thickness d of about 220 nm and a weight average molecular weight Mw of about 164,000.

Example 4

A cellulose membrane of Example 4 was prepared in the same manner as for the sample of Example 1 except that as the ionic liquid for dissolving cellulose, an ionic liquid in which $R_1$, $R_3$ and $R_4$ are methyl groups, and $R_2$ is an ethyl group in the general formula (s2) was used. The obtained cellulose membrane had a thickness d of about 200 nm and a weight average molecular weight Mw of about 162,000.

Example 5

A cellulose membrane of Example 5 was prepared in the same manner as for the sample of Example 1 except that as the ionic liquid for dissolving cellulose, an ionic liquid in which $R_1$ is a methyl group, and $R_2$, $R_3$ and $R_4$ are butyl groups in the general formula (s2) was used. The obtained cellulose membrane had a thickness d of about 200 nm and a weight average molecular weight Mw of about 167,000.

Example 6

A cellulose membrane of Example 6 was prepared in the same manner as for the sample of Example 1 except that as the ionic liquid for dissolving cellulose, 2-hydroxyethyltrimethyl ammonium 2,5-diaminopentanoate (choline ornithinate) in which $R_1$ is a hydroxyethyl group, $R_2$, $R_3$ and $R_4$ are methyl groups, n=4, $R_5$ is a hydrogen atom, one of $R_6$ is an amino group, and the remaining $R_6$ is a hydrogen atom in the general formula (s1) was used. The obtained cellulose membrane had a thickness d of about 190 nm and a weight average molecular weight Mw of about 170,000.

Example 7

A cellulose membrane of Example 7 was prepared in the same manner as for the sample of Example 1 except that as the cellulose to be dissolved in an ionic liquid, cellulose derived from bleached pulp made of wood having a purity of 95% or more was used. The obtained cellulose membrane had a thickness d of about 190 nm and a weight average molecular weight Mw of about 224,000. A contact angle with water of the obtained cellulose membrane was 7°. The contact angle was determined in the same manner as in Example 1.

Example 8

A cellulose membrane of Example 8 was prepared in the same manner as for the sample of Example 1 except that as the cellulose to be dissolved in an ionic liquid, cellulose derived from cotton having a purity of 95% or more was used. The obtained cellulose membrane had a thickness d of about 190 nm and a weight average molecular weight Mw of about 272,000. A contact angle with water of the obtained cellulose membrane was 2°. The contact angle was determined in the same manner as in Example 1.

Comparative Example 1

A cellulose membrane of Comparative Example 1 was prepared in the same manner as for the sample of Example 1 except that as the cellulose to be dissolved in an ionic liquid, microcrystalline cellulose (Avicel, "Avicel" is a registered trade name of FMC Corporation) was used. However, the polymer gel sheet got finely torn during the course of peeling off the polymer gel sheet from the glass substrate and removing the polymer gel sheet from the ultrapure water. A regenerated cellulose piece left with a certain degree of size had a weight average molecular weight Mw of about 30,800.

Comparative Example 2

A cellulose membrane of Comparative Example 2 was prepared in the same manner as for the sample of Example 1 except that as the cellulose to be dissolved in an ionic liquid, cellophane having a cellulose purity of 95% or more was used. However, the polymer gel sheet got finely torn during the course of peeling off the polymer gel sheet from the glass substrate and removing the polymer gel sheet from the ultrapure water. A regenerated cellulose piece left with a certain degree of size had a weight average molecular weight Mw of about 57,200.

Here, strength of each cellulose membrane was evaluated by holding the polymer gel sheet with tweezers and shaking light and left in the ultrapure water at the time of peeling off the polymer gel sheet from the glass substrate, and examining whether the shape of the membrane is kept. The result is shown in Table 1 below. "OK" in Table 1 indicates that in the remaining cellulose membrane, a total area of parts having an area that is equivalent or larger than the area of a circle of 3 mm in diameter was 80% or more of the area of the polymer gel sheet before peeling off, and "NG" indicates that a total area of parts having an area that is equivalent or larger than the area of a circle of 3 mm in diameter was less than 80% of the area of the polymer gel sheet before peeling off.

TABLE 1

|  | Weight average molecular weight Mw | Strength of membrane |
|---|---|---|
| Example 1 | 162,000 | OK |
| Example 2 | 152,000 | OK |
| Example 3 | 164,000 | OK |
| Example 4 | 162,000 | OK |
| Example 5 | 167,000 | OK |
| Example 6 | 170,000 | OK |
| Example 7 | 224,000 | OK |
| Example 8 | 272,000 | OK |
| Comparative Example 1 | 30,800 | NG |
| Comparative Example 2 | 57,200 | NG |

Table 1 reveals that any cellulose membrane having such a degree of strength required for self-supporting has a weight average molecular weight of about 150,000 or more.

(Evaluation of Formability)

Example 9

A cellulose membrane of Example 9 was prepared in the same manner as for the sample of Example 7 except that after dissolving cellulose in an ionic liquid, the cellulose solution was diluted in dimethyl sulfoxide, and the cellulose concentration in the cellulose solution and the size of the gap were adjusted so that the thickness of the regenerated cellulose membrane was a target thickness of 350 nm. The obtained cellulose membrane had a thickness d of about 370 nm.

Example 10

A cellulose membrane of Example 10 was prepared in the same manner as for the sample of Example 9 except that in place of the glass substrate, a polyethylene terephthalate (PET) substrate with a surface having a contact angle with water of 70° was used. The obtained cellulose membrane had a thickness d of about 350 nm.

Example 11

A cellulose membrane of Example 11 was prepared in the same manner as for the sample of Example 9 except that in place of the glass substrate, a polypropylene substrate having a corona-treated surface was used. The surface of the polypropylene substrate had a contact angle with water of 10°. The obtained cellulose membrane had a thickness d of about 360 nm.

Comparative Example 3

Preparation of a cellulose membrane of Comparative Example 3 was attempted in the same manner as for the sample of Example 9 except that in place of the glass substrate, a polyethylene (PE) substrate with a surface having a contact angle with water of 93° was used. However, the cellulose solution was repelled, and it was difficult to form a continuous liquid membrane on the polyethylene substrate.

Comparative Example 4

Preparation of a cellulose membrane of Comparative Example 4 was attempted in the same manner as for the sample of Example 9 except that in place of the glass substrate, a polypropylene substrate with a surface having a contact angle with water of 100° was used. However, the cellulose solution was repelled, and it was difficult to form a continuous liquid membrane on the polypropylene substrate.

Table 2 shows a contact angle with water in the substrate and formation of liquid membrane together for various substrates to which the cellulose solution is applied. In Table 2, "OK" indicates that the cellulose solution was not repelled on the substrate and a continuous liquid membrane was formed on the substrate stably for 1 h or more, and "NG" indicates that such a liquid membrane could not be formed on the substrate stably for 1 h or more.

TABLE 2

|  | Substrate | Contact angle with water | Formation of stable liquid membrane |
|---|---|---|---|
| Example 9 | Glass | 34° | OK |
| Example 10 | PET | 70° | OK |
| Example 11 | PP (with corona treatment) | 10° | OK |
| Comparative Example 3 | PE | 93° | NG |
| Comparative Example 4 | PP | 100° | NG |

Table 2 reveals that by using the substrate having a contact angle with water of 70° or less, it is possible to form a stable liquid membrane on the substrate.

(Evaluation of Appearance when Stuck to Skin)

Example 12

A cellulose membrane of Example 12 was prepared in the same manner as in Example 9 to have a target thickness of 100 nm, 200 nm, 500 nm, 600 nm, 900 nm, 1000 nm, or 1300 nm by adjusting the cellulose concentration in the cellulose solution and the size of the gap. Thickness d of the obtained cellulose membrane for each target thickness was about 90 nm, about 200 nm, about 540 nm, about 610 nm, about 890 nm, about 1050 nm, or about 1320 nm.

Comparative Example 5

A cellulose membrane of Comparative Example 5 was prepared in the same manner as in Example 9 to have a target thickness of 2 µm or 5 µm by adjusting the cellulose concentration in the cellulose solution and the size of the gap. Thickness d of each obtained cellulose membrane for each target thickness was about 2130 nm, or about 5 µm. For a sample having a target thickness more than 3 µm, the sample was placed on a surface plate, and measured for the thickness by using a digimatic indicator available from Mitutoyo Corporation in place of DEKTAK.

In the following manner, appearance when the cellulose membrane was stuck to skin was evaluated. First, a small amount of a commercially available toning lotion was applied on the skin of the inner side of the upper arm, and a cellulose membrane was stuck on the applied toning lotion. Then, whether the cellulose membrane was visible to the human eyes of another person at a distance of 30 cm was examined.

Figure 14:
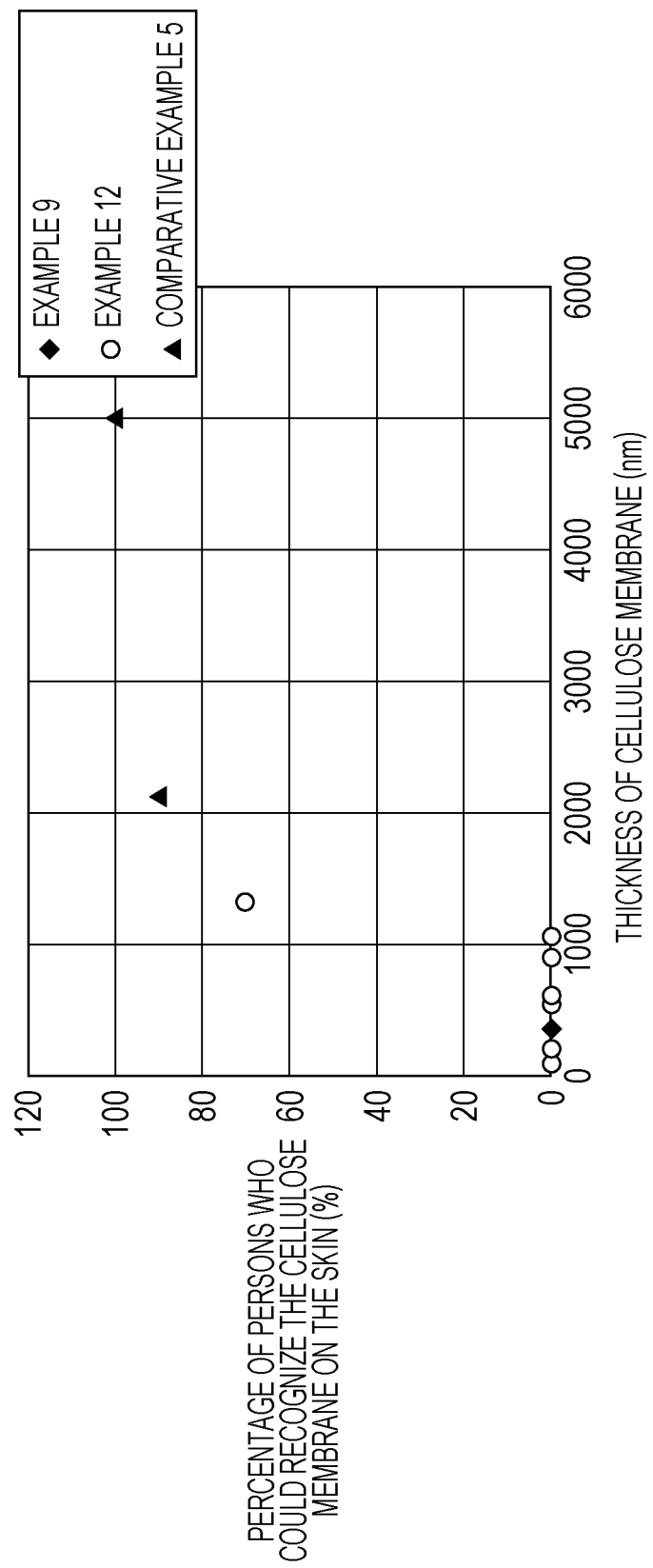
FIG. 14 is a graph showing evaluation results of appearance when the cellulose membrane is stuck to skin concerning cellulose membranes of various thicknesses in Examples 9, 12 and Comparative Example 5.

FIG. 14 is a graph showing evaluation results concerning cellulose membranes of various thicknesses in Example 12 and Comparative Example 5. In the graph of FIG. 14, the vertical axis indicates percentage of persons who could recognize the cellulose membrane on the skin among 25 persons of different sexes aged 20s to 50s observing the cellulose membrane on the skin. FIG. 14 also shows the result of evaluation for the cellulose membrane of Example 9. FIG. 14 reveals that by setting the thickness to be about 1000 nm or less, it is possible to provide a cellulose membrane that is less conspicuous even when stuck to the skin.

(Evaluation of Adhesiveness)

Comparative Example 6

By dissolving polylactic acid having a weight average molecular weight of 250,000 in chloroform, a 1.5 wt % polylactic acid solution was prepared. After applying the polylactic acid solution by spin coating (rotation speed: 2000 rpm) on a substrate on which a polyvinyl alcohol film having a weight average molecular weight of about 500 was preliminarily formed, the chloroform which was a solvent was vaporized. Thereafter, polyvinyl alcohol was removed by immersing in water to prepare a polylactic acid membrane of Comparative Example 6. The obtained polylactic acid membrane had a thickness d of about 410 nm.

Comparative Example 7

A polylactic acid membrane of Comparative Example 7 was prepared in the same manner as in Comparative Example 6 except that the concentration of polylactic acid in the polylactic acid solution was 2.4 wt %. The obtained polylactic acid membrane had a thickness d of about 960 nm. A contact angle with water of the obtained polylactic acid membrane was 79°. The contact angle was determined in the same manner as in Example 1.

In the following manner, adhesiveness when the cellulose membrane was stuck to skin was evaluated. First, a small amount of a commercially available toning lotion was applied on the skin of the inner side of the upper arm, and a sample (cellulose membrane or polylactic acid membrane) was stuck on the applied toning lotion. After a lapse of 5 h in that condition, whether the sample fell off the skin was examined.

Figure 15:
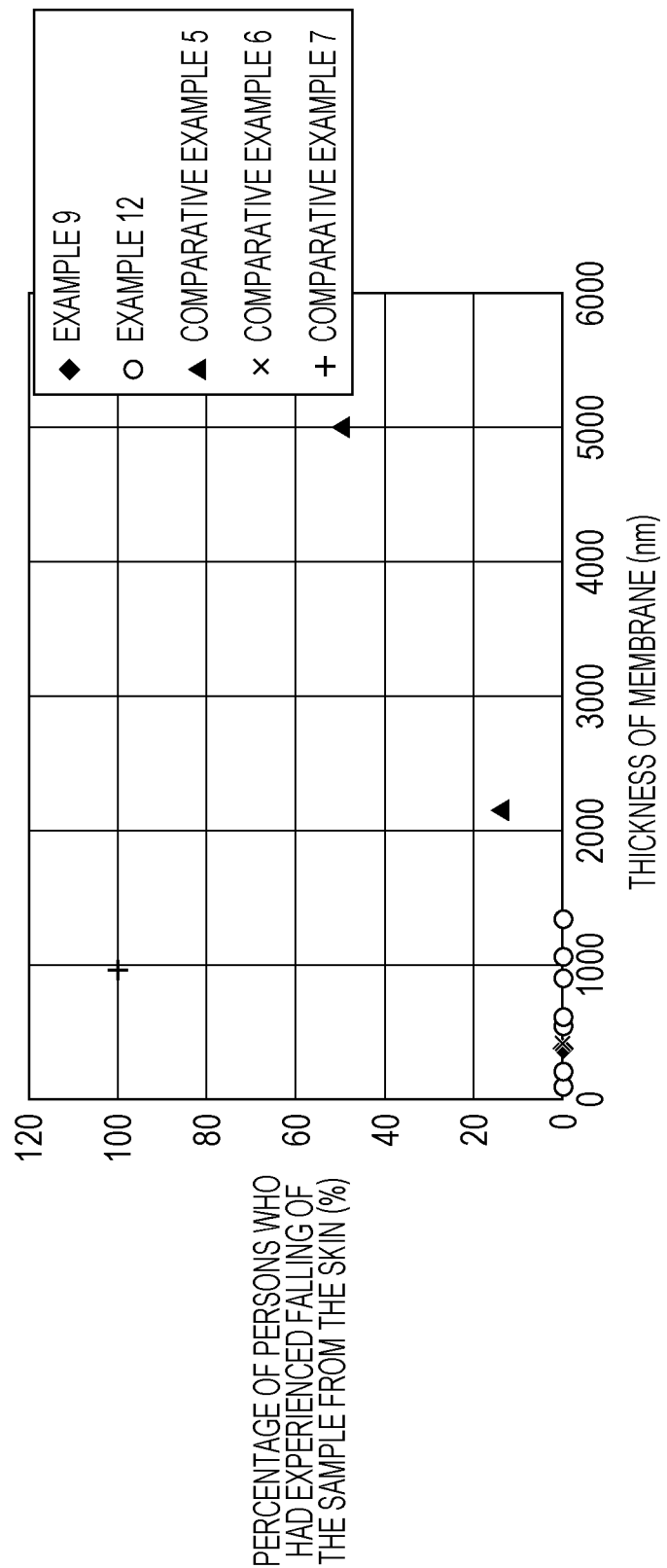
FIG. 15 is a graph showing evaluation results of adhesiveness concerning samples of Examples 9, 12 and Comparative Examples 5 to 7.

FIG. 15 is a graph showing evaluation results concerning samples of Examples 9, 12 and Comparative Examples 5 to 7. In the graph of FIG. 15, the vertical axis indicates percentage of persons who had experienced falling of the sample among the persons to whom a sample was stuck (6 persons in total). FIG. 15 reveals that by setting the thickness to be about 1300 nm or less when cellulose is used as a material for the membrane, it is possible to provide a thin membrane that is less likely to fall off from the skin, namely that is excellent in adhesiveness with skin. Also, comparison between the polylactic acid membrane (thickness: about 960 nm) of Comparative Example 7, and the cellulose membrane (thickness: about 890 nm) having a thickness close to the thickness of the polylactic acid membrane of Comparative Example 7, among the cellulose membranes of Example 12 revealed that cellulose is more advantageous than polylactic acid from the view point of obtaining a thin membrane that is less likely to fall off from the skin. Also, among the cellulose membranes of Example 12, falling off from the skin was not observed in the cellulose membranes having thicknesses of about 1050 nm and about 1320 nm that are larger than the thickness of the polylactic acid membrane of Comparative Example 7. In other words, it can be said that a thin membrane having high adhesiveness with skin is obtained easily by using cellulose rather than polylactic acid as a material.

(Evaluation of Tensile Strength)

Example 13

A cellulose membrane of Example 13 was prepared in the same manner as for the sample of Example 7 except that a cellulose solution was prepared by dissolving cellulose in a mixture of an ionic liquid and dimethyl sulfoxide, and the cellulose concentration in the cellulose solution and the size of the gap were adjusted so that the thickness of regenerated cellulose membrane was a target thickness of 1000 nm. The obtained cellulose membrane had a thickness d of about 970 nm. The obtained cellulose membrane had a degree of crystallinity of 0%. Water vapor transmission rate of the cellulose membrane of Example 13, measured by a method according to JIS K7129-C in the same manner as for the water vapor transmission rate concerning plastic film and sheet was $3.8 \times 10^4$ g/m$^2 \cdot$24 h. A contact angle with water of the obtained cellulose membrane was 10°. The contact angle was determined in the same manner as in Example 1.

Example 14

A cellulose membrane of Example 14 was prepared in the same manner as for the sample of Example 13 except that after applying a liquid membrane on the glass substrate, and before gelating the liquid membrane, the liquid membrane was heated for 2 h in an environment at 70° C. under a reduced pressure of about 0.02 MPa. The obtained cellulose membrane had a thickness d of about 990 nm. The water vapor transmission rate measured in the same manner for the sample of Example 13 was $1.2 \times 10^4$ g/m$^2 \cdot$24 h. A contact angle with water of the obtained cellulose membrane was 28°. The contact angle was determined in the same manner as in Example 1.

Figure 16:
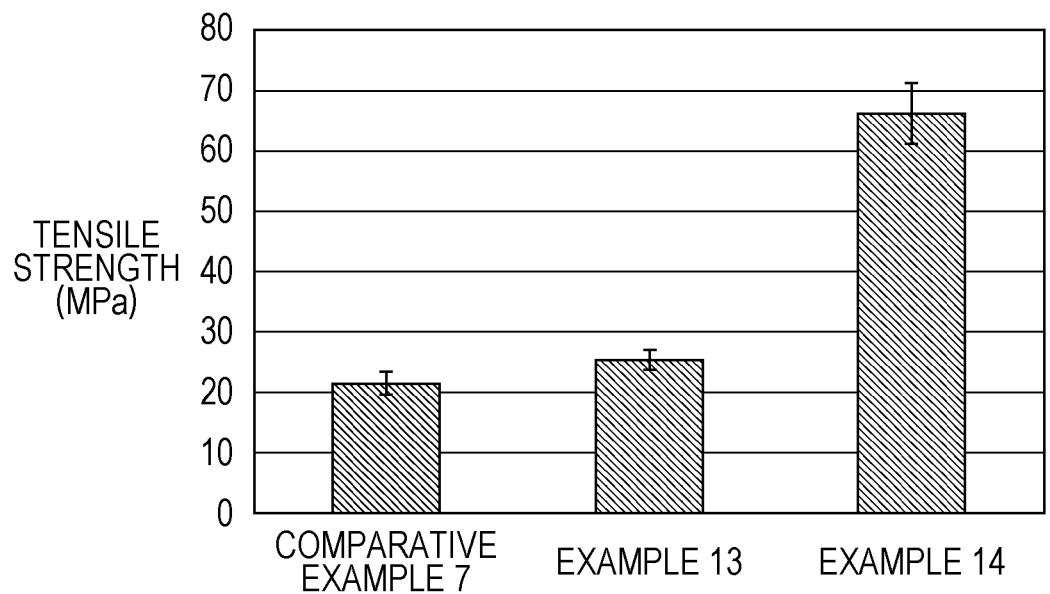
FIG. 16 is a graph showing evaluation results of tensile strength concerning samples of Examples 13, 14 and Comparative Example 7.

FIG. 16 shows evaluation results of tensile strength concerning samples of Examples 13, 14 and Comparative Example 7. Tensile strengths of cellulose membrane and polylactic acid membrane can be measured by a method according to JISK 7161. For measurement, a sample prepared by drying for 2 h or more in an environment at about 0.02 MPa, 90° C., and cutting into a shape of No. 7 test piece was used. For measurement of tensile strength, for example, a compact table-top tester EZ-Test available from Shimadzu Corporation was used, and measurement was conducted for a plurality of test pieces under the conditions of temperature: 23° C., distance between chucks: 20 mm, and stress rate: 1 mm/min, and evaluation was made by an average value.

As shown in FIG. 16, comparison between Comparative Example 7 and Example 13 revealed that the regenerated cellulose thin membrane can have a tensile strength that is comparable to or higher than that of polylactic acid thin membrane. The result of measurement concerning Example 14 reveals that the step of heating the liquid membrane provides the effect of improving the tensile strength.
(General Evaluation)

Example 15

A cellulose membrane of Example 15 was prepared in the same manner as for the sample of Example 13 except that the step of gelating the liquid membrane was omitted. The obtained cellulose membrane had a thickness d of about 1000 nm and a degree of crystallinity of 12%. The XRD pattern concerning the cellulose of the cellulose membrane of Example 15 did not have a peak peculiar to the crystal structure I, and the cellulose of the cellulose membrane of Example 15 had the crystal structure II. The water vapor transmission rate measured in the same manner for the sample of Example 13 was $3.3 \times 10^4$ g/m²·24 h. A contact angle with water of the obtained cellulose membrane was 7°. The contact angle was determined in the same manner as in Example 1.

Example 16

A cellulose membrane of Example 16 was prepared in the same manner as for the sample of Example 9 except that the liquid membrane was gelated under a saturated vapor pressure of ethanol at 25° C. The obtained cellulose membrane had a thickness d of about 350 nm.

Example 17

A cellulose membrane of Example 17 was prepared in the same manner as for the sample of Example 9 except that the liquid membrane was gelated under a saturated vapor pressure of tert-butyl alcohol at 25° C. The obtained cellulose membrane had a thickness d of about 350 nm.

Example 18

A cellulose membrane of Example 18 was prepared in the same manner as for the sample of Example 13 except that the degree of crystallinity was adjusted by gelating the liquid membrane in an environment of 80 to 90% RH. The obtained cellulose membrane had a thickness d of about 990 nm and a degree of crystallinity of 5%. The XRD pattern concerning the cellulose of the cellulose membrane of Example 18 did not have a peak peculiar to the crystal structure I, and the cellulose of the cellulose membrane of Example 18 had the crystal structure II. A contact angle with water of the obtained cellulose membrane was 7°. The contact angle was determined in the same manner as in Example 1.

Example 19

A cellulose membrane of Example 19 having a size of 8 cm square was prepared in the same manner as for the sample of Example 9 except that the cellulose solution was applied on the glass substrate by slot die coating. The obtained cellulose membrane had a thickness d of about 400 nm.

Example 20

A cellulose membrane of Example 20 was prepared in the same manner as for the sample of Example 9 except that in the step of drying the polymer gel sheet, freeze-drying was conducted after the polymer gel sheet was immersed in tert-butyl alcohol. The obtained cellulose membrane had a thickness d of about 1000 nm and a bulk density of 0.5 g/cm³.

Example 21

A cellulose membrane of Example 21 was prepared by immersing the cellulose membrane of Example 20 in an aqueous solution of collagen, and then removing water by drying under heating at 40° C. Retainment of collagen in the cellulose membrane was confirmed by the attenuated total reflection (ATR) method using a Fourier-transform infrared spectroscopic analyzer Frontier IR available from PerkinElmer, Inc.

Example 22

The cellulose membrane of Example 22 was prepared in the same manner as in Example 21 except that an aqueous solution of vitamin C was used in place of the aqueous solution of collagen. Retainment of vitamin C in the obtained cellulose membrane was confirmed by the infrared spectroscopy in the same manner as in Example 21.

Example 23

The cellulose membrane of Example 23 was prepared in the same manner as in Example 21 except that a solution of vitamin E in ethanol was used in place of the aqueous solution of collagen. Retainment of vitamin E in the obtained cellulose membrane was confirmed by the infrared spectroscopy in the same manner as in Example 21.

Comparative Example 8

A cellulose membrane of Comparative Example 8 was prepared in the same manner as for the sample of Example 9 except that the concentration of the cellulose solution and the size of the gap were adjusted so that the thickness of the regenerated cellulose membrane was a target thickness of 20 nm. The obtained cellulose membrane on the glass substrate had a thickness d of 17 nm. It was difficult to lift up the cellulose membrane of Comparative Example 8 with tweezers without breaking down the form of the membrane.

Comparative Example 9

Preparation of a cellulose membrane of Comparative Example 9 was attempted in the same manner as for the sample of Example 1 except that the liquid membrane was formed by using a suspension having a cellulose concentration of 2 wt % prepared by mixing cellulose nanofiber available from SUGINO MACHINE LIMITED and water. However, the form of the membrane broke down in the washing of the polymer gel sheet, and a thin membrane was not obtained.

The following Table 3 shows evaluation results of formation of a self-supporting thin membrane, adhesiveness with skin, and stress to skin, concerning Examples 1 to 11 and 13 to 23, and Comparative Examples 6 to 9. Adhesiveness to skin was evaluated in the following method. First, for each of three subjects, a small amount of a commercially available toning lotion was applied on the skin of the inner side of the upper arm, and a sample (cellulose membrane or polylactic acid membrane) was stuck on the applied toning lotion. After a lapse of 8 h in that condition, whether the sample fell off the skin was examined. In Table 4, "NG" indicates that the sample fell off from the skin before a lapse of 8 h in any subject. Stress to skin was evaluated in the following manner. For each of three subjects, a small amount of water was applied on the skin of the inner side of the upper arm, and a sample was stuck on the applied water. After a lapse of 1 h in that condition, whether there was a subject who had strangeness such as sweatiness or reddened skin, or felt a trouble, in the three subjects was examined. In Table 3, "NG" indicates that there was a subject who had unpleasantness or felt a trouble.

TABLE 3

| | Polymer material | Formation of self-supporting thin membrane | Adhesiveness to skin (8 h) | Stress to skin (Presence or absence of unpleasantness) |
|---|---|---|---|---|
| Example 1 | Regenerated cellulose | OK | OK | OK |
| Example 2 | Regenerated cellulose | OK | OK | OK |
| Example 3 | Regenerated cellulose | OK | OK | OK |
| Example 4 | Regenerated cellulose | OK | OK | OK |
| Example 5 | Regenerated cellulose | OK | OK | OK |
| Example 6 | Regenerated cellulose | OK | OK | OK |
| Example 7 | Regenerated cellulose | OK | OK | OK |
| Example 8 | Regenerated cellulose | OK | OK | OK |
| Example 9 | Regenerated cellulose | OK | OK | OK |
| Example 10 | Regenerated cellulose | OK | OK | OK |
| Example 11 | Regenerated cellulose | OK | OK | OK |
| Example 13 | Regenerated cellulose | OK | OK | OK |
| Example 14 | Regenerated cellulose | OK | OK | OK |
| Example 15 | Regenerated cellulose | OK | OK | OK |
| Example 16 | Regenerated cellulose | OK | OK | OK |
| Example 17 | Regenerated cellulose | OK | OK | OK |
| Example 18 | Regenerated cellulose | OK | OK | OK |
| Example 19 | Regenerated cellulose | OK | OK | OK |
| Example 20 | Regenerated cellulose | OK | OK | OK |
| Example 21 | Regenerated cellulose | OK | OK | OK |
| Example 22 | Regenerated cellulose | OK | OK | OK |
| Example 23 | Regenerated cellulose | OK | OK | OK |
| Comparative Example 6 | Polylactic acid | OK | OK | NG |
| Comparative Example 7 | Polylactic acid | OK | NG | NG |
| Comparative Example 8 | Regenerated cellulose | NG | — | — |
| Comparative Example 9 | Cellulose Nanofiber | NG | — | — |

For example, comparison between the cellulose membrane of Example 13 (thickness: 970 nm) and the polylactic acid membrane of Comparative Example 7 (thickness: 960 nm) having almost the same thickness revealed that the sample of Example 13 using cellulose is less likely to add stress to skin than the sample of Comparative Example 7 using polylactic acid. That is, it is found that as a material for thin membrane, cellulose is more advantageous for long-term use. As can be seen from the evaluation results of stress to skin, cellulose is more advantageous than polylactic acid from the view point of suppressing sweatiness or the like. The result shown in Table 3 reveals that according to the embodiment of the present disclosure, it is possible to prepare a self-supporting regenerated cellulose membrane that adds less stress to skin, and has excellent adhesiveness to skin.

As described in the above, according to an embodiment of the present disclosure, a self-supporting cellulose membrane is provided. While the cellulose membrane does not require a support for keeping the form, the cellulose membrane and the support may be integrated, for example, for convenience of storage and carrying.

INDUSTRIAL APPLICABILITY

The cellulose membrane according to an embodiment of the present disclosure can be stuck on skin without an adhesive, and less likely to give a user a sensation of being stuck on the skin. Also, the cellulose membrane is less likely to add stress to skin even when it is stuck to skin for a long time. The cellulose membrane can be stuck to skin, an organ and the like. Cellulose membrane can be used, for example, as a skin protective film or a skin care film intended for cosmetics or medical care. Also it is possible to make the cellulose membrane retain a component that acts on living organism or protects living organism such as a cosmetic component, or may be provided with color or a pattern, and the multilayer sheet of the present disclosure can also be used as a functional sheet for protection or decoration as well as for cosmetics or medical cares, for example.

REFERENCE SIGNS LIST

100, 100a, 100b: cellulose membrane
100A, 100B: multilayer sheet
101, 102: protective layer
120: polymer gel sheet
140: substrate
200: skin
300: liquid
302: cream

The invention claimed is:

1. A membrane for sticking to a living organism, wherein
the membrane is capable of keeping a form of the membrane without a support,
the membrane is formed of regenerated cellulose having a weight average molecular weight of 150,000 or more, and
the membrane has a thickness of between 20 nm and 1300 nm, inclusive.

2. The membrane for sticking to a living organism according to claim 1, wherein
the membrane has an area of 7 mm² or more.

3. The membrane for sticking to a living organism according to claim 1, wherein
the membrane has a tensile strength of 23 MPa or more.

4. The membrane for sticking to a living organism according to claim 1, wherein
the membrane has a water vapor transmission rate of $1 \times 10^4$ g/m²·24 h or more.

5. The membrane for sticking to a living organism according to claim 1, wherein
the membrane has a contact angle with water of 30° or less.

6. The membrane for sticking to a living organism according to claim 1, wherein
the membrane has a degree of crystallinity between 0% and 12%, inclusive.

7. The membrane for sticking to a living organism according to claim 1, wherein
the membrane has a bulk density between 0.3 g/cm³ and 1.5 g/cm³, inclusive.

8. The membrane for sticking to a living organism according to claim 1, wherein
a component acting on living organism or a component protecting living organism is retained by at least a part inside the membrane.

9. The membrane for sticking to a living organism according to claim 1, wherein
a coloring component is retained by at least a part inside the membrane, and
the membrane is used as cosmetics or medical supplies.

10. A multilayer sheet comprising:
the membrane according to claim 1; and
a first protective layer disposed on one of principal surfaces of the membrane for sticking to living organism,
wherein the first protective layer is detachable from the one of principal surfaces.

11. The multilayer sheet according to claim 10, further comprising:
a second protective layer disposed on the other of the principal surfaces of the membrane for sticking to living organism.

* * * * *